United States Patent [19]

Kasai et al.

[11] Patent Number: 4,771,068
[45] Date of Patent: Sep. 13, 1988

[54] MITOMYCIN DERIVATIVES HAVING ANTI-TUMOR AND ANTIBACTERIAL UTILITY

[75] Inventors: Masaji Kasai, Fujisawa; Yutaka Saito, Machida; Motomichi Kono, Machida; Akira Sato, Machida; Hiroshi Sano, Machida; Kunikatsu Shirahata, Komae; Makoto Morimoto, Shizuoka; Tadashi Ashizawa, Numazu, all of Japan

[73] Assignee: Kyowa Hakko Kogyo Kabushiki Kaisha, Japan

[21] Appl. No.: 850,200

[22] Filed: Apr. 10, 1986

[30] Foreign Application Priority Data

Apr. 10, 1985 [JP] Japan .................................. 60-76047
Sep. 24, 1985 [JP] Japan ................................ 60-210441
Dec. 3, 1985 [JP] Japan ................................ 60-271742

[51] Int. Cl.$^4$ ..................... A61K 31/40; C07D 487/14
[52] U.S. Cl. ..................................... 514/410; 548/422
[58] Field of Search ......................... 548/422; 514/410

[56] References Cited

U.S. PATENT DOCUMENTS

| | | | |
|---|---|---|---|
| 3,332,944 | 7/1967 | Cosulich et al. | 548/422 X |
| 4,268,676 | 5/1981 | Remers | 548/181 |
| 4,567,256 | 1/1986 | Vyas et al. | 544/357 X |
| 4,617,389 | 10/1986 | Remers | 544/372 X |

FOREIGN PATENT DOCUMENTS

| | | |
|---|---|---|
| 0116208 | 6/1983 | European Pat. Off. . |
| 1795473 | 3/1972 | Fed. Rep. of Germany . |
| 38-7958 | 8/1960 | Japan . |
| 45-3099 | 2/1970 | Japan . |
| 56-73085 | 6/1981 | Japan . |
| 56-92288 | 7/1981 | Japan . |
| 57-188590 | 11/1982 | Japan . |
| 59-1486 | 1/1984 | Japan . |
| 59-104386 | 6/1984 | Japan . |
| 59-175493 | 10/1984 | Japan . |
| 59-205382 | 11/1984 | Japan . |
| 2106096 | 4/1983 | United Kingdom . |
| 2140799 | 4/1984 | United Kingdom . |
| 2140779 | 12/1984 | United Kingdom . |

OTHER PUBLICATIONS

Iyengar et al., Chem. Abstracts, vol. 98 (1983), entry 16475t.
The Merck Index, Tenth Ed., 1983-pp. 890, 891 and 1097.
The Journal of Antibiotics, vol. XXI, No. 3, Mar. 1968, pp. 189–198.
J. Med. Chem. 1983, vol. 26, No. 1, pp. 16–20.

Primary Examiner—Donald G. Daus
Assistant Examiner—William A. Teoli, Jr.
Attorney, Agent, or Firm—Wolder, Gross & Yavner

[57] ABSTRACT

Mitomycin derivatives of the formula:

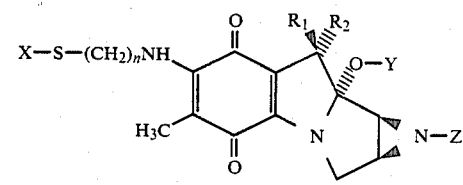

wherein X is

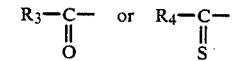

[wherein $R_3$ is alkyl, cycloalkyl or optionally substituted phenyl; and $R_4$ is alkyl or cycloalkyl]; n is an integer of 2 to 8; one of $R_1$ and $R_2$ is a hydrogen atom and the other is a carbamoyloxymethyl group, or alternatively $R_1$ and $R_2$ may be combined together to form a methylene group ($=CH_2$); and Y and Z independently represent hydrogen or methyl;

exhibit anti-bacterial and anti-tumor activities.

6 Claims, No Drawings

MITOMYCIN DERIVATIVES HAVING ANTI-TUMOR AND ANTIBACTERIAL UTILITY

The present invention relates to novel mitomycin derivatives having antibacterial and anti-tumour activities.

Mitomycins are generally known as antibiotics having antibacterial and anti-tumour activities. For example, mitomycin A, mitomycin B, mitomycin C and porfiromycin are descried in Merck Index, 10th Edition. Mitomycin C is practically used for treating and curing human cancers in Japan and various countries of the world. Examples of the known mitomycins are shown in the following Tables 1 and 2.

TABLE 1

Mitomycins derived from natural sources

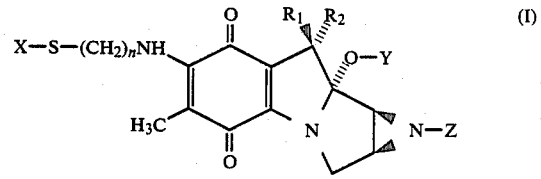

| | $X_A$ | $Y_A$ | $Z_A$ | $R_A$ | $R_B$ |
|---|---|---|---|---|---|
| Mitomycin | | | | | |
| A | $OCH_3$ | $CH_3$ | H | $CH_2OCONH_2$ | H |
| B | $OCH_3$ | H | $CH_3$ | H | $CH_2OCONH_2$ |
| C | $NH_2$ | $CH_3$ | H | $CH_2OCONH_2$ | H |
| D | $NH_2$ | H | $CH_3$ | H | $CH_2OCONH_2$ |
| E | $NH_2$ | $CH_3$ | $CH_3$ | H | $CH_2OCONH_2$ |
| F | $OCH_3$ | $CH_3$ | $CH_3$ | $CH_2OCONH_2$ | H |
| G | $NH_2$ | $CH_3$ | $CH_3$ | * | |
| H | $OCH_3$ | H | $CH_3$ | * | |
| J | $OCH_3$ | $CH_3$ | $CH_3$ | H | $CH_2OCONH_2$ |
| K | $OCH_3$ | $CH_3$ | $CH_3$ | * | |
| Porfiromycin | $NH_2$ | $CH_3$ | $CH_3$ | $CH_2OCONH_2$ | H |

*$R_A$ and $R_B$ are combined together to form $=CH_2$.

TABLE 2

Mitomycins obtained by semi-synthesis

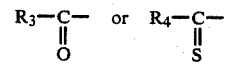

| Mitomycin | $X_A$ | $Y_A$ | $Z_A$ | $R_A$ | $R_B$ |
|---|---|---|---|---|---|
| (1) | $NH_2$ | H | $CH_3$ | * | |
| (2) | $NH_2$ | $CH_3$ | H | * | |
| (3) | $OCH_3$ | $CH_3$ | H | * | |
| (4) | $OCH_3$ | H | $CH_3$ | $CH_2OCONH_2$ | H |
| (5) | $NH_2$ | H | $CH_3$ | $CH_2OCONH_2$ | H |

Notes:
(1) 9a-O—demethylmitomycin G
(2) 1a-demethylmitomycin G
(3) 1a-demethylmitomycin K
(4) 9-epi-mitomycin B
(5) 9-epi-mitomycin D
*$R_A$ and $R_B$ are combined together to form $=CH_2$.

Although mitomycins have excellent anti-tumour activity, they exhibit undesired side effects such as decrease of leucocytes. With such a background, various mitomycin derivatives have hitherto bee synthesized for the purpose of increasing their activity and/or reducing their toxicity. Examples of these mitomycin derivatives include those in which the 7-amino group is substituted with a substituent containing at least one sulphur atom.

For example, mitomycin C and porfiromycin in which the 7-amino group is substituted with 2-mercaptoethyl group or a 2-(ethylthio)ethyl group (GB 2106096A, Japanese Published Unexamined Patent Application No. 188590/82), mitomycins in which the 7-amino group is substituted with a 2-(substituted dithio)ethyl group (EP 0116208A1, Japanese Published Unexamined Patent Application Nos. 104386/84 and 175493/84, GB 2140799A, and Japanese Published Unexamined Patent Application No. 205382/84), and mitomycin derivatives of symmetrical disulfide type such as 7-N, 7'-N'-dithiodiethylenedimitomycin C (EP 0116208A1, and Japanese Published Unexamined Patent Application Nos. 104386/84 and 175493/84) have been known.

We have sought mitomycin derivatives having improved properties, and have found that mitomycin derivatives in which the 7-amino group is substituted with an (ω-acylthio)alkyl group or an (ω-dithioacyloxy)alkyl group have excellent antibacterial and anti-tumour activities with low toxicity. Mitomycin derivatives having such a substituent are novel compounds and are structurally very distinct from the afore-mentioned derivatives.

The present invention provides mitomycin derivatives represented by the following formula (I):

$$X-S-(CH_2)_nNH \cdots \quad (I)$$

wherein X is $$R_3-\underset{\underset{O}{\|}}{C}- \quad \text{or} \quad R_4-\underset{\underset{S}{\|}}{C}-$$

[wherein $R_3$ is an alkyl group having 1 to 8 carbon atoms, a 3-6 membered cycloalkyl group, or a phenyl group optionally bearing 1-5 substituents selected from lower alkyl, hydroxy, lower alkoxy, nitro, lower alkylamino, di-lower alkylamino, lower alkanoylamino, cyano or halogen; and $R_4$ is an alkyl group having 1 to 8 carbon atoms or a 3-6 membered cycloalkyl group]; n is an integer of 2 to 8; one of $R_1$ and $R_2$ is a hydrogen atom and the other is a carbamoyloxymethyl group, or alternatively $R_1$ and $R_2$ may be combined together to form a methylene group ($=CH_2$); and Y and Z independently represent hydrogen or methyl.

The compound(s) of the formula (I) are hereinafter referred to as Compound(s) (I). Compounds represented by other formulae are also designated similarly.

With regard to the definition of $R_3$ and $R_4$ in the formula (I), the alkyl group having 1 to 8 carbon atoms may be the straight chain or branched alkyl group having 1 to 8 carbon atoms such as methyl, ethyl, n-propyl, i-propyl, n-butyl, n-pentyl, n-hexyl, n-heptyl and n-octyl groups. In the definition of $R_3$ and $R_4$, the 3-6 membered cycloalkyl group is exemplified by cyclopentyl and cyclohexyl groups.

With regard to the definition of the substituent of the substituted phenyl group, the lower alkyl group includes straight chain or branched alkyl groups having 1 to 5 carbon atoms such as methyl, ethyl, i-propyl, n-butyl and n-pentyl groups; the lower alkoxyl group includes alkoxy groups having 1 to 3 carbon atoms such as methoxy, ethoxy and i-propoxy groups; the lower alkylamino group includes straight chain or branched alkylamino groups having 1 to 4 carbon atoms such as methylamino group; the di-lower alkylamino group includes straight chain or branched dialkylamino groups having 1 to 4 carbon atoms such as dimethylamino and diethylamino groups; the lower alkanoylamino group includes alkanoylamino groups having 1 to 3 carbon atoms such as formamido, acetamido and n-propionamido groups; and the halogen atom includes fluorine, chlorine, bromine, etc.

These substituents may be the same or different and the number of the substituents may be 1 to 2. Preferred examples of the substituents are the case where the number of the substituents is 1 or 2 and the substituents may be the same or different and selected from the lower alkyl, hydroxy, lower alkoxy, nitro, lower alkylamino, lower alkanoylamino, cyano groups and halogen atoms. The specific examples of the substituted phenyl groups are 3-chlorophenyl, 4-bromophenyl, 4-fluorophenyl, 4-methoxyphenyl, 2-methylphenyl, 4-nitrophenyl, 4-cyanophenyl, 4-t-butylphenyl, 3-dimethylaminophenyl, 2-hydroxyphenyl and 4-acetamido-4-fluorophenyl groups.

A compound (I) may be prepared by the reaction of a compound of the formula (II):

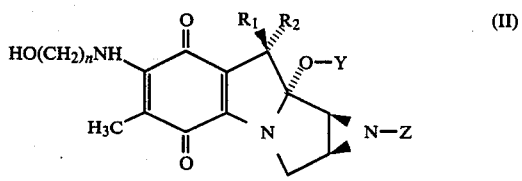

(wherein n, $R_1$, $R_2$, Y and Z are as defined in the formula (I)), with a compound of the formula (III):

(wherein X is as defined in the formula (I)) in an inert solvent and in the presence of triphenylphosphine and dialkyl azodicarboxylate.

The solvents which may be used for this reaction are anhydrous solvents and exemplified by diethyl ether, tetrahydrofuran and other ether solvents, benzene, methylene chloride, hexamethylphosphoroustriamide and the like, which may be used alone or in combination.

The dialkyl azodicarboxylate includes diethyl azodicarboxylate, diisopropyl azodicarboxylate, etc.

One equivalent each of Compound (III), triphenylphosphine and dialkyl azodicarboxylate based on Compound (II) is sufficient, but up to about 3 equivalents may be used, in order to increase the yield from Compound (II).

The reaction temperature and the reaction time may vary with Compound (II) or (III) used, but usually, the reaction is carried out at a temperature of −20° to 30° C. and completed in several minutes to about one hour.

The treatment after the reaction may vary with Compound (III) used. But usually, the reaction solution is directly concentrated under reduced pressure. Alternatively, the reaction solution is extracted with a water-insoluble solvent such as chloroform, methylene chloride, ethyl acetate or the like, and the extract is washed with water, aqueous sodium bicarbonate, etc. and concentrated. Then, either concentrate is purified by column chromatography, thin layer chromatography, recrystallization and the like.

Compound (II) may be synthesized by the reaction of a mitomycin derivative having an alkoxy, acyloxy or di-lower alkylaminomethyleneimino group at the 7-position with an ω-hydroxyalkylamine.

The reaction of a mitomycin having an acyloxy group at the 7-position with an amine is disclosed in Japanese Published Unexamined Patent Application No. 73085/81, and the reaction of a mitomycin having a di-lower alkylaminomethyleneimino group at the 7-position with an amine is disclosed in Japanese Published Unexamined Patent Application No. 1486/84.

However, it is preferred to use a mitomycin having an alkoxy group at the 7-position, particularly a 7-methoxymitomycin. The reaction of a 7-methoxymitomycin with an alkylamine is disclosed in, for example, J. Antobiot., 189 (1968). Examples of 7-methyoxymitomycins are mitomycins A, B, F, H, J and K, 1a-demethylmitomycin K, 9-epi-mitomycin B and the like, as shown in Tables 1 and 2. Such a 7-methoxymitomycin reacts with an ω-hydroxyalkylamine to produce a Compound (II) in good yield.

Any inert solvent may be used so long as it can dissolve the mitomycin used as starting material, and dimethylformamide, dimethylsulfoxide, methanol, ethanol and other alcohols, ethylene glycol, monomethyl ether and the like may preferably be used solely or in combination. Usually, the reaction may be effected at room temperature, even though the reaction proceeds with heating or cooling. The reaction time may vary, depending upon the mitomycin and ω-hydroxyalkylamine used as raw materials, and usually the reaction is completed in several ten minutes to several hours. The reaction product viz. Compound (II) may be purified by column chromatography, recrystallization and the like.

A compound of the formula (I) wherein X is

[hereinafter referred to as Compound(s) (I-1)] may also be prepared by the reaction of a mitomycin derivative represented by the formula (IV):

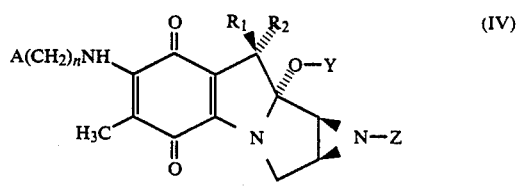

(wherein A is a halogen atom, an unsubstituted or substituted alkanesulfonyloxy group, or an unsubstituted or substituted benzenesulfonyloxy group; and n, $R_1$, $R_2$, Y and Z are as defined in the formula (I)) with a metal salt of thiocarboxylic acid represented by the formula

(wherein $R_3$ is as defined in the formula (I) and M is an alkali metal or an alkaline earth metal) in an inert solvent.

This process for preparation of Compounds (I-1) is generally superior to the afore-mentioned process for preparation of Compounds (I-1) from Compounds (II) because according to the former process by-products derived from the starting materials or reagents are less compared with the latter process, and thus purification and isolation of Compound (I-1) are easy.

With regard to the definition of A in the formula (IV), the halogen atom includes a chlorine, bromine, iodine atom, etc.; the unsubstituted or substituted alkanesulfonyloxy group includes a methanesulfonyloxy, trifluoromethanesulfonyloxy group, etc.; the unsubstituted or substituted benzenesulfonyloxy group includes a benzenesulfonyloxy, p-toluenesulfonyloxy group, etc. Further, with regard to the definition of M in the formula (V), the alkali metal includes lithium, sodium, potassium, etc., and the alkaline earth metal includes magnesium, etc. When M is divalent metal such as magnesium, etc., compounds of the formula (V) are represented by $[(R_3COS)_2Mg]$, etc.

Chloroform, methylenedichloride, diethyl ether, tetrahydrofuran, dioxane, ethylene glycol dimethyl ether, dimethylsulfoxide, dimethylformamide, etc. are used alone or in combination as the inert solvent. The reaction temperature and reaction time vary with Compound (IV) or (V) used or with the concentration of Compound (V), and the reaction may generally be carried out at $-10°$ to $50°$ C. and completed in several minutes to several hours.

Purification and isolation of Compound (I-1) may be carried out in the same manner as explained in those of Compound (I) in production of Compound (I) from Compound (II).

Compound (IV), a starting material for synthesis of Compound (I-1) may be synthesized by the reaction of a mitomycin derivative having an alkoxy, acyloxy or di-lower alkylaminomethyleneimino group at the 7-position with a compound represented by the formula (VI):

$$A(CH_2)_nNH_2 \quad (VI)$$

(wherein, A and n are as defined in the formulae (IV) and (I), respectively) or an acid adduct salt thereof in an inert solvent. When an acid adduct salt of Compound (VI) such as hydrochloride, hydrobromide and substituted benzenesulfonate is used, the acid which liberates should be neutralized with a tertiary amine such as triethylamine, pyridine and N,N-dimethylaniline.

Any inert solvent may be used so long as it can dissolve the mitomycin used as starting material, and dimethylformamide, dimethylsulfoxide, methanol, ethanol and other alcohols, ethylene glycol monomethyl ether and the like may preferably be used solely or in combination. Usually, the reaction may be effected at room temperature, even though the reaction proceeds with heating or cooling. The reaction time may vary, depending upon the mitomycin and Compound (VI) used as starting materials, and usually the reaction is completed in several ten minutes to several hours. Compound (IV) may be purified by column chromatography, thin layer chromatography, recrystallization and the like.

Further, a compound of the formula (IV) wherein A is an unsubstituted or substituted alkanesulfonyloxy group, or an unsubstituted or substituted benzenesulfonyloxy group, and Z is a methyl group may also be prepared by the reaction of a compound of the formula (II) wherein Z is a methyl group with an unsubstituted or substituted alkanesulfonyl halide, an unsubstituted or substituted benzenesulfonyl halide, or an acid anhydride, respectively corresponding to the group A in an inert solvent in the presence of a base.

The halide and acid anhydride used include methanesulfonyl chloride, trifluoromethanesulfonyl chloride, trifluoromethanesulfonic anhydride, benzenesulfonyl chloride, p-toluenesulfonyl chloride, etc. The base includes triethylamine, pyridine, etc. The inert solvent includes dimethylformamide, dimethylsulfoxide, tetrahydrofuran, chloroform, etc., and these solvents are used solely or in combination. Pyridine can be used as the base as well as the solvent.

The reaction may be carried out at $0°$ C. to room temperature. The reaction temperature varies with the nature and number of equivalents of the sulfonyl halide used; usually, the reaction is complete in a few hours to about 10 hours. After the completion of the reaction, the reaction solution is diluted with a water-insoluble solvent such as chloroform, methylene chloride and ethyl acetate, washed with aqueous sodium bicarbonate and concentrated. The concentrate is purified by column chromatography, thin layer chromatography, recrystallization and the like.

Compounds (II) are new compounds except those of the following combinations of the groups:

(1) $n=2$, $R_1=CH_2OCONH_2$, $R_2=H$, $Y=CH_3$ and $Z=H$;

(2) $n=2$, $R_1=H$, $R_2=CH_2OCONH_2$, $Y=H$ and $Z=CH_3$;

(3) $n=3$, $R_1=CH_2OCONH_2$, $R_2=H$, $Y=CH_3$ and $Z=H$;

(4) $n=3$, $R_1=CH_2OCONH_2$, $R_2=H$, $Y=CH_3$ and $Z=CH_3$;

(5) $n=2$, $R_1=H$, $R_2=CH_2OCONH_2$, $Y=CH_3$ and $X=CH_3$.

Compounds (II) in case of the above combinations are disclosed or embraced in Japanese Published Examined Patent Application No. 3099/70 or 7958/63 or Japanese Published Unexamined Patent Application No. 1486/84 or 92288/81 or U.S. Pat. No. 3,332,944.

Further, Compounds (IV) are new compounds except those of the following five combinations of the groups:

(1) $A=Cl$, $n=2$, $R_1=CH_2OCONH_2$, $R_2=H$, $Y=CH_3$ and $Z=H$;

(2) $A=Cl$, $n=2$, $R_1=CH_2OCONH_2$, $R_2=H$, $Y=CH_3$ and $Z=CH_3$; and (3) $A=Cl$, $n=3$, $R_1=CH_2OCONH_2$, $R_2=H$, $Y=CH_3$ and $Z=H$.

(4) $A=F$, $n=2$, $R_1=CH_2OCONH_2$, $R_2=H$, $Y=CH_3$ and $Z=H$ (5) $A=F$, $n=2$, $R_2=CH_2OCONH_2$, $R_2=H$, $Y=CH_3$ and $Z=CH_3$.

Compounds (IV) in case of the above (1)-(5) are disclosed in Japanese Published Unexamined Patent Application No. 92288/81; (4) and (5) are disclosed in J. Med. Chem. Vol. 26, No. 1, pages 16-20 (1983).

Compounds (I) have excellent antibacterial and anti-tumour activities and are useful as antibacterial agents or anti-tumour agents. Compounds (I) generally show an enhanced anti-tumour activity and/or reduced bone marrow toxicity in comparison with mitomycin C. That is, Compounds (I) generally have a higher chemotherapeutic index (i.e., LD$_{50}$/ED$_{50}$) or WBC$_{4000}$ (i.e., the minimum dose of a chemical which reduces the peripheral leucocytes number to 4000/mm$^3$) than mitomycin C.

In Compounds (I) wherein X is

and R$_3$ is an alkyl group having 1 to 8 carbon atoms, Compounds (I) wherein R$_3$ is an alkyl group having 1 to 4 carbon atoms, above all, a methyl or ethyl group are preferred from the viewpoint of anti-tumour activity. Further, Compounds (I) wherein X is

R$_3$ is a methyl or ethyl group and n is 2 or 3 are generally water-soluble. Such a water-soluble Compound (I) has enhanced utility for intravenous and intraarterial injections.

On the other hand, Compounds (I) wherein R$_3$ is an unsubstituted or substituted phenyl group and Compounds (I) wherein X is

are generally fat-soluble.

The pharmacological properties of Compounds (I) were assessed by the following tests.

EXPERIMENT 1

Antibacterial activities of Compounds (I) against various bacteria are shown by the minimum growth inhibitory concentration (μg/ml) in Table 3. The minimum growth inhibitory concentration was measured at pH 7.0 according to the agar dilution method. In the table, bacteria are indicated by the following letters.

SF: *Streptococcus faecalis* ATCC 10541
SA: *Staphylococcus aureus* ATCC 6538P
BS: *Bacillus subtilis* 10707
PV: *Proteus vulgaris* ATCC 6897
KP: *Klebsiella pneumoniae* ATCC 10031

Chemical structures of test compounds are shown in the following Table 8.

TABLE 3

| Compound | Antibacterial activity (minimum growth inhibitory concentration, μg/ml) | | | | |
|---|---|---|---|---|---|
| | SF | SA | BS | PV | KP |
| 1 | <0.020 | <0.020 | <0.020 | 1.3 | 0.078 |
| 2 | 3.1 | 3.1 | 0.78 | 25 | 6.3 |
| 3 | 0.039 | 0.078 | <0.02 | 20 | 1.3 |
| 4 | >100 | 50 | 6.3 | 100 | 25 |
| 5 | <0.020 | <0.020 | <0.020 | 1.3 | 0.31 |
| 6 | 13 | 13 | 0.78 | 100 | 25 |
| 7 | <0.020 | 0.039 | <0.020 | 2.5 | 0.31 |
| 8 | 50 | >100 | 13 | — | — |
| 9 | <0.020 | 0.039 | <0.020 | 5 | 0.31 |
| 10 | 0.039 | 0.078 | 0.078 | 5 | 1.3 |
| 11 | 0.16 | 0.16 | 0.16 | 2.5 | 1.3 |
| 12 | 5 | 0.31 | 0.31 | 5 | 1.3 |
| 13 | 0.039 | <0.020 | <0.020 | 5 | 1.3 |
| 14 | 50 | >100 | 0.39 | — | >100 |
| 15 | >100 | 25 | 1.6 | 25 | 50 |
| 16 | 0.63 | 0.16 | 0.078 | >40 | 10 |

TABLE 3-continued

| Compound | Antibacterial activity (minimum growth inhibitory concentration, μg/ml) | | | | |
|---|---|---|---|---|---|
| | SF | SA | BS | PV | KP |
| 17 | 2.5 | 0.63 | 0.16 | >40 | 10 |
| 18 | 0.16 | <0.020 | <0.020 | 10 | 5 |
| 19 | 100 | 6.3 | 1.6 | — | — |
| 20 | 0.63 | 0.63 | 0.31 | >40 | 40 |
| 21 | 0.039 | <0.020 | <0.020 | 5 | 1.3 |
| 22 | 25 | 0.39 | <0.049 | — | >100 |
| 23 | 0.16 | <0.020 | <0.020 | 10 | 5 |
| 24 | 100 | 1.6 | 1.6 | — | — |
| 25 | 13 | 3.1 | 0.39 | >100 | 13 |
| 26 | <0.020 | <0.020 | <0.020 | 0.63 | 0.078 |
| 27 | 0.39 | 0.20 | <0.049 | 3.1 | 0.78 |
| 28 | 0.039 | <0.020 | <0.020 | 2.5 | 1.3 |
| 29 | >100 | 3.1 | 1.6 | 13 | 25 |
| 30 | 0.31 | 0.31 | 0.31 | 5 | 1.3 |
| 31 | 2.5 | 1.3 | 2.5 | 10 | 2.5 |

EXPERIMENT 2

Anti-tumour activity against Sarcoma 180 solid tumour and toxicity.

Taking some of Compounds (I) as examples, anti-tumour activity (ED$_{50}$) against Sarcoma 180 solid tumour and acute toxicity (LD$_{50}$) as well as effect on peripheral leucocytes number (WBC$_{4000}$) are shown in Table 4.

TABLE 4

| Compound | Anti-tumour activity and toxicity | | | | |
|---|---|---|---|---|---|
| | LD$_{50}$ (mg/kg) | ED$_{50}$ (mg/kg) | CI | CI$_c$ | WBC$_{4000}$ (mg/kg) |
| 1 | 5.6 | 2.3 | 2.4 | 1.2 | 9.5 |
| 2 | 26.3 | 5.6 | 4.7 | 1.9 | 14.1 |
| 3 | 9.4 | 5.6 | 1.7 | 0.88 | 11.0 |
| 4 | 45 | 14.9 | 3.0 | 1.6 | 27.1 |
| 5 | 4.7 | 5.0 | 0.94 | 0.59 | >5 |
| 7 | 11.3 | 5.2 | 2.2 | 0.88 | >25 |
| 9 | 90 | 21.7 | 4.1 | 1.6 | 65.2 |
| 10 | >75 | 37.5 | >2.0 | >1.1 | >75 |
| 11 | >200 | 27.0 | >7.4 | 3.9 | 31.3 |
| 12 | 45 | 9.7 | 4.6 | 1.3 | 19.6 |
| 13 | 6.0 | 4.1 | 1.5 | 0.91 | >5 |
| 15 | ≧50 | 27.5 | ≧1.8 | ≧0.74 | 27.5 |
| 17 | >50 | 9.5 | >5.3 | >1.7 | 32.2 |
| 18 | 6.0 | 1.6 | 3.8 | 1.2 | 5 |
| 19 | 15.0 | 5.6 | 2.7 | 0.89 | 19.1 |
| 20 | 62.5 | 16.3 | 3.8 | 1.6 | 13.0 |
| 21 | 9.4 | 2.0 | 4.7 | 1.9 | 11.5 |
| 23 | 6.3 | 2.5 | 2.5 | 0.81 | 5 |
| 24 | 27.5 | 7.2 | 3.8 | 1.3 | 25.5 |
| 25 | 33.8 | 6.9 | 4.9 | 1.6 | 15.9 |
| 26 | 6.6 | 1.2 | 5.5 | 1.6 | 7.6 |
| 27 | 13.1 | 3.4 | 3.9 | 1.1 | 15.5 |
| 28 | 13.1 | 3.3 | 4.0 | 1.1 | 10.4 |
| 30 | >100 | 37.7 | >2.7 | >1.1 | 58.1 |
| 31 | >100 | 28.1 | >3.6 | >1.5 | 27.5 |
| MMC | 8.4 | 2.4–5.3 | 1.6–3.5 | 1 | 2.4–6.1 |

CI: LD$_{50}$/ED$_{50}$
CI$_c$: Value given by division of CI of each test compound by CI of mitomycin C as control determined in the same condition as in the determination of anti-tumour activity of the test compound. A CI$_c$ value greater than 1 means that the range of therapeutically effective dose of the test compound is greater than that of mitomycin C.
WBC$_{4000}$: Minimum dose of a test compound which reduces the peripheral leucocytes number to 4000/mm$^3$.
MMC: mitomycin C The experiments were performed according to the following procedures.

(1) Effect against Sarcoma 180 solid tumour cells $5 \times 10^6$ cells of Sarcoma 180 solid tumour were intraperitoneally implanted into ddY mice. 7 days later, ascites cells were sampled. The cells were washed once with a sterilized physiological sodium chloride solution and were used to prepare a cell suspension containing $5 \times 10^7$ cells per ml with a sterilized physiological sodium chloride solution. On each occasion, 0.1 ml of the cell suspension was subcutaneously implanted into the right axilla of a male mouse (ddY strain; body weight $20 \pm 2$ g). The test compound was dissolved in a physiological sodium chloride solution with or without addition of Tween 80 and was administered into the tail vein of each mouse of a group consisting of 5 mice at a dose of 0.1-0.2 ml, 24 hours after the implantation of the tumour cells.

The anti-tumour activity was determined in the following manner. 7 days after the implantation, the major axis (a) and the minor axis (b) of the tumour were measured to calculate a value of "$a \times b^2/2$" which corresponds to the volume of the tumour. The anti-tumour activity was expressed by the ratio (T/C) of the volume (T) of the tumours of the group of animals administered with the test compound to the corresponding volume (C) of tumours of the untreated animals.

(2) Determination of $ED_{50}$ $ED_{50}$ shows the amount of a substance needed for reducing the volume of Sarcoma 180 solid tumours in mice to 50% on the basis of the corresponding volume of Sarcoma solid tumours in control animals.

On graph paper, T/C was indicated by an arithmetic scale on the longitudinal axis and the administered amount of the test compound was indicated by a logarithmic scale on the lateral axis. The relationship between the dose and T/C was shown by a straight line determined by the method of least squares, from which a dose corresponding to T/C of 0.5 was obtained.

(3) Acute toxicity

Each animal of the test group consisting of 5 ddY mice was administered intraperitoneally once with a test compound. After the administration, the animals were observed for 14 days and deaths were noted. The $LD_{50}$ was determined by Beherns Kaerber's method.

(4) Effect on the peripheral leucocytes number

Sarcoma 180 solid tumour cells ($5 \times 10^6$) were subcutaneously implanted into the right axilla of each mouse (body weight $20 \pm 2$ g) of a group consisting of 5 male mice (ddY strain). 24 hours after implantation, a test compound was intraperitoneally administered to each animal. 4 days after the administration, blood (each 0.02 ml) was collected from the suborbital plexus vein of each tumour-carrying animal. The collected sample of blood was dispersed in 9.98 ml of Cell-Kit Seven solution. One drop of saponin solution was added to the sample to dissolve erythrocytes and then a microcell counter was used to count the number of leucocytes. On graph paper, the number of leucocytes was indicated by an arithmetic scale on the longitudinal axis and the dose of the test compound was indicated by a logarithmic scale on the lateral axis. The relationship between the number of peripheral leucocytes and the dose of the test compound was plotted and the dose (i.e., $WBC_{4000}$) corresponding to 4000 peripheral leucocytes/mm$^3$ (about half the number of leucocytes of normal mice) was obtained.

EXPERIMENT 3

Experiment as to solubility of some of Compounds (I) in water 1 mg of a test compound was added to 100 μl of 0.03M phosphate buffer (pH 7.0). The mixture was stirred at 22° C. for 15 minutes and filtered through Ekicrodisc 3 (disposable filter unit, Gelman Sciences Japan Co.) to remove insoluble matters. The filtrate is a saturated solution of the test compound. Predetermined amount of the saturated solution was injected into a high performance liquid chromatograph [column: YMC-A212 ($C_8$) φ6 mm, 150 mm, eluting solvent: 0.01M-ammonium acetate/methanol, wave length for detection: 254 nm] and peak area of the chromatogram was calculated. Separately, a solution of the test compound in methanoL having a certain concentration of the compound was similarly subjected to the chromatography to make the calibration curve. The solubility of the test compound was calculated by the calibration curve.

The results are shown in Table 5.

TABLE 5

| Compound | Solubility (mg/ml) | Compound | Solubility (mg/ml) |
| --- | --- | --- | --- |
| 1 | 5.6 | 10 | 1.0 |
| 2 | 8.9 | 11 | 0.21 |
| 3 | 3.8 | 13 | 0.073 |
| 4 | 1.9 | 21 | 0.0047 |
| 7 | 3.5 | 26 | 0.26 |
| 8 | 9.6 | MMC | 1.9 |
| 9 | 2.0 | | |

Thus, according to a further feature of the present invention, there are provided pharmaceutical compositions containing as an active ingredient at least one Compound (I) in association with one or more pharmaceutical carriers and/or excipients.

For use as, for example, anti-tumour agents for mammals including human beings, Compound (I) may be dissolved, for example, in physiological sodium chloride solution, or a glucose, lactose or mannitol injection solution. Administration may be effected, for example, by intravenous injection at a dose of 0.06-5 mg/kg of body weight for one day. Compound (I) may be freeze-dried in accordance with the Pharmacopoeia of Japan and a dry powder injectable formulation may be prepared with addition of sodium chloride. The anti-tumour agent may further contain well-known pharmacologically acceptable diluent(s), adjuvant(s) and/or carrier(s) such as salts which fulfil pharmaceutical utility. The dose of a pharmaceutical composition according to the invention may be varied depending upon, for example, the age and symptoms of each patient. The administration schedule may be varied depending upon the dose. Thus, administration may be effected, for example, at intervals of one or three weeks. If desired, oral or rectal administration is also possible, e.g. using the above doses, for which purpose tablets, capsules, powders, granules, suppositories, etc. containing appropriate excipients may be used. If desired, intraarterial, intraperitoneal and intrapleural administrations may also be possible using the above doses. Anti-tumour agents of the present invention are expected to be usable for treating chronic lymphocytic leukemia, chronic myelogenous leukemia, cancer of the breast, gastric cancer, cancer of the liver, carcinoma of the colon, cancer of the rectum, lung cancer, cancer of the pancreas, carcinoma colli, carcinoma corporis, head and neck cancer and so on. The proper content of Compound (I) in the anti-tumour agents of the present invention is 0.01–20 mg in 20–50 ml when used as injections, and is 0.001–85 weight percent when used as tablets, capsules, powders, granules, suppositories, etc.

Certain specific embodiments of the present invention are illustrated by the following examples and reference examples. Physicochemical data of each compound were obtained by using the following devices.

IR: Shimadzu IR-27-G (measured by KBr method)
NMR: JEOL FX-100 Spectrometer (100 MHz) or Bruker AM400 Spectrometer (400 MHz). Solvents used were $CDCl_3$ in Compounds (I) wherein X is

and pyridine-$d_5$ in the other Compounds (I).
MS: Hitachi M-80B Mass Spectrometer (EI method or SI method)
M.P.: Yanagimoto micro melting point apparatus (hot plate)

TLC: Merck Art 5714 (silica gel plate)

Chemical structures of Compounds (II) and (IV) used in the following examples are shown in Tables 6 and 7, and chemical structures of typical Compounds (I) are shown in Table 8.

TABLE 6

Chemical structures of typical Compounds (II)

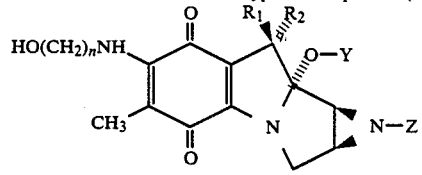

(II)

| Compound | n | $R_1$ | $R_2$ | Y | Z |
|---|---|---|---|---|---|
| a | 2 | $CH_2OCONH_2$ | H | $CH_3$ | H |
| b | 2 | H | $CH_2OCONH_2$ | H | $CH_3$ |
| c | 2 | $CH_2OCONH_2$ | H | $CH_3$ | $CH_3$ |
| d | 2 | $=CH_2$ | | H | $CH_3$ |
| e | 3 | $CH_2OCONH_2$ | H | $CH_3$ | H |
| f | 3 | $CH_2OCONH_2$ | H | $CH_3$ | $CH_3$ |
| g | 3 | H | $CH_2OCONH_2$ | H | $CH_3$ |
| h | 4 | $CH_2OCONH_2$ | H | $CH_3$ | H |
| i | 5 | $CH_2OCONH_2$ | H | $CH_3$ | H |
| j | 6 | $CH_2OCONH_2$ | H | $CH_3$ | H |
| k | 8 | $CH_2OCONH_2$ | H | $CH_3$ | H |

TABLE 7

Chemical structures of typical Compounds (IV)

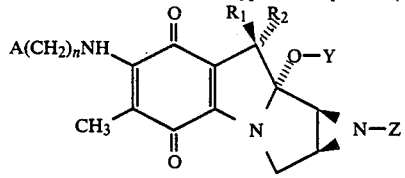

(IV)

| Compound | A | n | $R_1$ | $R_2$ | Y | Z |
|---|---|---|---|---|---|---|
| l | Br | 2 | $CH_2OCONH_2$ | H | $CH_3$ | H |
| m | Cl | 2 | $CH_2OCONH_2$ | H | $CH_3$ | H |
| n | Cl | 3 | $CH_2OCONH_2$ | H | $CH_3$ | H |
| o | Cl | 2 | H | $CH_2OCONH_2$ | H | $CH_3$ |
| p | $CH_3SO_2-O-$ | 3 | H | $CH_2OCONH_2$ | H | $CH_3$ |
| q | 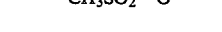 | 6 | $CH_2OCONH_2$ | H | $CH_3$ | H |
| r | Br | 8 | $CH_2OCONH_2$ | H | $CH_3$ | H |

TABLE 8

Chemical structures of typical Compounds (I)

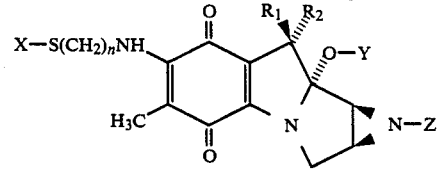

(I)

| Compound | X | n | $R_1$ | $R_2$ | Y | Z |
|---|---|---|---|---|---|---|
| 1 | $CH_3CO$ | 2 | $CH_2OCONH_2$ | H | $CH_3$ | H |
| 2 | $CH_3CO$ | 2 | H | $CH_2OCONH_2$ | H | $CH_3$ |
| 3 | $CH_3CO$ | 2 | $CH_2OCONH_2$ | H | $CH_3$ | $CH_3$ |
| 4 | $CH_3CO$ | 2 | $=CH_2$ | | H | $CH_3$ |
| 5 | $CH_3CH_2CO$ | 2 | $CH_2OCONH_2$ | H | $CH_3$ | H |
| 6 | $CH_3CH_2CO$ | 2 | H | $CH_2OCONH_2$ | H | $CH_3$ |
| 7 | $CH_3CO$ | 3 | $CH_2OCONH_2$ | H | $CH_3$ | H |
| 8 | $CH_3CO$ | 3 | H | $CH_2OCONH_2$ | H | $CH_3$ |
| 9 | $CH_3CO$ | 4 | $CH_2OCONH_2$ | H | $CH_3$ | H |

TABLE 8-continued

Chemical structures of typical Compounds (I)

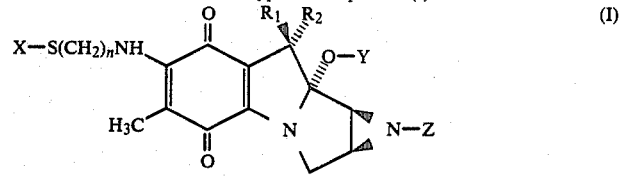

| Compound | X | n | $R_1$ | $R_2$ | Y | Z |
|---|---|---|---|---|---|---|
| 10 | $CH_3CO$ | 5 | $CH_2OCONH_2$ | H | $CH_3$ | H |
| 11 | $CH_3CO$ | 6 | $CH_2OCONH_2$ | H | $CH_3$ | H |
| 12 | $CH_3CO$ | 8 | $CH_2OCONH_2$ | H | $CH_3$ | H |
| 13 | Bz | 2 | $CH_2OCONH_2$ | H | $CH_3$ | H |
| 14 | Bz | 2 | H | $CH_2OCONH_2$ | H | $CH_3$ |
| 15 | Bz | 2 | =$CH_2$ | | H | $CH_3$ |
| 16 | Bz | 2 | $CH_2OCONH_2$ | H | $CH_3$ | $CH_3$ |
| 17 | Bz | 6 | $CH_2OCONH_2$ | H | $CH_3$ | H |
| 18 | 4-F—Bz | 2 | $CH_2OCONH_2$ | H | $CH_3$ | H |
| 19 | 4-F—Bz | 2 | H | $CH_2OCONH_2$ | H | $CH_3$ |
| 20 | 4-F—Bz | 8 | $CH_2OCONH_2$ | H | $CH_3$ | H |
| 21 | 4-Br—Bz | 2 | $CH_2OCONH_2$ | H | $CH_3$ | H |
| 22 | 4-Br—Bz | 2 | H | $CH_2OCONH_2$ | H | $CH_3$ |
| 23 | 4-$CH_3O$—Bz | 2 | $CH_2OCONH_2$ | H | $CH_3$ | H |
| 24 | 4-$CH_3O$—Bz | 2 | H | $CH_2OCONH_2$ | H | $CH_3$ |
| 25 | 4-$NO_2$—Bz | 2 | H | $CH_2OCONH_2$ | H | $CH_3$ |
| 26 | $CH_3CS$ | 2 | $CH_2OCONH_2$ | H | $CH_3$ | H |
| 27 | $CH_3CS$ | 2 | H | $CH_2OCONH_2$ | H | $CH_3$ |
| 28 | $CH_3CS$ | 2 | $CH_2OCONH_2$ | H | $CH_3$ | $CH_3$ |
| 29 | $CH_3CS$ | 2 | =$CH_2$ | | H | $CH_3$ |
| 30 | $CH_3CS$ | 4 | $CH_2OCONH_2$ | H | $CH_3$ | H |
| 31 | $CH_3CS$ | 6 | $CH_2OCONH_2$ | H | $CH_3$ | H |

Bz: Benzoyl

EXAMPLE 1

7-N-[(2-acetylthio)ethyl]mitomycin (Compound 1)

257.1 mg of triphenylphosphine (hereinafter referred to as TPP) and 193 μl of diisopropyl azodicarboxylate (hereinafter referred to as DIAD) were dissolved in 2.0 ml of anhydrous tetrahydrofuran. The solution was stirred for 30 minutes in nitrogen atmosphere under cooling with ice water. To this solution was added 2 ml of anhydrous THF solution containing 185.3 mg of Compound 1 and 70.1 μl of thioacetic acid, and the solution was stirred further for 15 minutes with ice-cooling. Then the reaction solution was diluted with ethyl acetate (50 ml), followed by washing with a saturated aqueous solution of sodium bicarbonate. After removal of the ethyl acetate layer, the layer of the aqueous sodium bicarbonate solution was extracted three times with ethyl acetate (each 50 ml). The ethyl acetate layers were combined, washed with a saturated aqueous sodium bicarbonate solution and a saturated aqueous sodium chloride solution, and then dried over anhydrous sodium sulfate. After removal of the drying agent by filtration, solvent was evaporated under reduced pressure. The residue was chromatographed by using a column packed with silica gel (60 g). Elution was effected with a solvent system of chloroform/acetone/methanol (70:25:5). By TLC using the same solvent system as above, blue fractions showing an Rf value of 0.34 were collected and combined.

After evaporating the solvent under reduced pressure, the residue was dissolved in a small amount of chloroform and powderized with addition of n-hexane. The solvent was evaporated under reduced pressure, and the residue was held at room temperature under reduced pressure to remove the solvent adequately, whereby Compound 1 (180.7 mg; 84.6%) was obtained as grayish blue powder.

Starting material, reagent, appearance, yield, M.P. and MS of Compound 1 and Compounds 2–12 synthesized in the same manner as described above are shown in Table 9, and IR and NMR of these compounds in Table 10.

TABLE 9

| Synthesis and physical properties of typical Compounds (I) | | | | | |
|---|---|---|---|---|---|
| Starting materials and reagents | Product | Appearance | Yield (%) | M.P. (°C.) | M S (EI) |
| C No. a (185 mg) TA (70 μl) TPP (257 mg), DIAD (193 μl) | C No. 1 | Grayish blue powder | 84.6 | 57.0–64.0 | $M^+$ = 436 (436, 1429) $C_{19}H_{24}N_4O_6S$ = 436, 1415 |
| C No. b (200 mg) TA (95 μl) TPP (347 mg), DIAD (261 μl) | C No. 2 | Green powder | 81.1 | 83.0–87.5 | $M^+$ = 436 (436, 1442) $C_{19}H_{24}N_4O_6S$ = 436, 1415 |
| C No. c (182 mg) TA (83 μl) TPP (304 mg), DIAD (228 μl) | C No. 3 | Dark blue powder | 95.5 | 57.0–62.0 | $M^+$ = 450 $C_{20}H_{26}N_4O_6S$ = 450 |
| C No. d (99 mg) TA (56 μl) TPP (204 mg), DIAD (153 μl) | C No. 4 | Brown powder | 85.1 | 67.0–73.0 | $M^+$ = 375 $C_{18}H_{21}N_3O_4S$ = 375 |
| C No. a (284 mg) | C No. 5 | Dark | 65.0 | 49.0–55.0 | $M^+$ = 450 |

TABLE 9-continued
Synthesis and physical properties of typical Compounds (I)

| Starting materials and reagents | Product | Appearance | Yield (%) | M.P. (°C.) | M S (EI) |
|---|---|---|---|---|---|
| TP (166 μl) TPP (492 mg), DIAD (369 μl) | | bluish purple powder | | | $C_{20}H_{26}N_4O_6S = 450$ |
| C No. b (196 mg) TP (114 μl) TPP (340 mg), DIAD (255 μl) | C No. 6 | Grayish green powder | 50.8 | 77.0–79.5 | $M^+ = 450$ $C_{20}H_{26}N_4O_6S = 450$ |
| C No. e (260 mg) TA (118 μl) TPP (435 mg), DIAD (326 μl) | C No. 7 | Dark bluish purple powder | 63.1 | 69.0–75.0 | $M^+ = 450$ $C_{20}H_{26}N_4O_6S = 450$ |
| C No. g (196 mg) TA (89 μl) TPP (328 mg), DIAD (246 μl) | C No. 8 | Grayish green powder | 95.0 | 79.0–82.0 | $M^+ = 450$ $C_{20}H_{26}N_4O_6S = 450$ |
| C No. h (207 mg) TA (73 μl) TPP (267 mg), DIAD (200 μl) | C No. 9 | Dark bluish purple powder | 64.2 | 56.0–65.0 | $M^+ = 464$ $C_{21}H_{28}N_4O_6S = 464$ |
| C No. i (97 mg) TA (41 μl) TPP (152 mg), DIAD (114 μl) | C No. 10 | Dark bluish purple powder | 61.4 | 47.5–51.0 | $M^+ = 478$ $C_{22}H_{30}N_4O_6S = 478$ |
| C No. j (254 mg) TA (84 μl) TPP (307 mg), DIAD (230 μl) | C No. 11 | Dark bluish purple powder | 63.9 | 40.5–45.0 | $M^+ = 492$ $C_{23}H_{32}N_4O_6S = 492$ |
| C No. k (231 mg) TA (89 μl) TPP (328 mg), DIAD (246 μl) | C No. 12 | Dark bluish purple solid | 43.2 | 40.0–43.0 | $M^+ = 520$ $C_{25}H_{36}N_4O_6S = 520$ |

Notes:
C No. ... Compound No.
TA ... Thioacetic acid
TP ... Thiopropionic acid

TABLE 10
IR and NMR data of typical Compounds (I)

| Compound | IR (cm$^{-1}$) | N M R (δ) |
|---|---|---|
| 1 | 3300, 2940, 1718, 1690, 1632, 1555, 1508, 1445, 1324, 1060 | (100MHz) about 2.1(1H, m), 2.10(3H, s), 2.26(3H, s), 2.74(1H, bm), about 3.1(1H, m), 3.16(2H, t, J=6.5), 3.21(3H, s), 3.59(1H, dd, J=12.7, 2.2), 3.78(2H, q, J=6.5), 3.98(1H, dd, J=11.0, 4.4), 4.51(1H, d, J=12.7), 5.05(1H, t, J=10.8), 5.38(1H, dd, J=10.5, 4.4), 7.19 (1H, t, J=6.5), 7.63(2H, bs). |
| 2 | 3370, 3300, 1692, 1632, 1549, 1510, 1450, 1332, 1111, 1057 | (100MHz) 2.06(3H, s), 2.12(3H, s), 2.22(1H, dd, J=4.6, 2.2), 2.24(3H, s), 2.46(1H, d, J=4.6), 3.11(2H, t, J=6.8), 3.66(1H, dd, J=12.9, 2.2), 3.72(2H, q, J=6.8), 4.22(1H, dd, J=9.8, 3.7), 4.42(1H, d, J=12.9), 5.21 (1H, t, J=10.2), 5.48(1H, dd, J=10.5, 3.7), 7.19(1H, t, J=6.8), 7.48(2H, bs), 8.34(1H, bs). |
| 3 | 3450, 3300, 2950, 1720, 1690, 1632, 1557, 1508, 1447, 1324, 1060 | (100MHz) 2.12(3H, s), 2.15(1H, dd, J=4.6, 2.0), 2.24 (3H, s), 2.26(3H, s), 2.53(1H, d, J=4.6), 3.18(2H, t, J=6.8), 3.18(3H, s), 3.52(1H, dd, J=12.9, 2.0), 3.79 (2H, q, J=6.8), 3.94(1H, dd, J=11.2, 4.4), 4.44(1H, d, J=12.9), 4.77(1H, t, J=10.9), 5.31(1H, dd, J=10.5, 4.4), 7.23(1H, t, J=6.8), 7.68(2H, bs). |
| 4 | 3360, 3270, 1687, 1637, 1531, 1508, 1462, 1441, 1109, 1048 | (100MHz) 2.04(3H, s), 2.15(3H, s), 2.24(2H, s), 2.27 (1H, dd, J=4.6, 1.5), 2.62(1H, d, J=4.6), 3.09(2H, t, J=7.0), 3.71(2H, q, J=6.8), 3.73(1H, dd, J=12.7, 1.5), 4.71(1H, d, J=12.7), 5.81(1H, d, J=1.2), 6.49 (1H, d, J=1.2), 7.24(1H, t, J=6.8), 8.89(1H, bs). |
| 5 | 3440, 3290, 1713, 1630, 1556, 1509, 1445, 1324, 1060 | (400MHz) 1.06(3H, t, J=7.5), 2.09(1H, bt, J=8.0), 2.11(3H, s), 2.53(2H, q, J=7.5), 2.75(1H, bs), 3.14 (1H, bs), 3.19(2H, t, J=6.7), 3.22(3H, s), 3.59(1H, bd, J=12.7), 3.79(2H, q, J=6.7), 3.99(1H, dd, J=11.2, 4.2), 4.51(1H, d, J=12.7), 5.08(1H, bt, J=10.8), 5.38(1H, dd, J=10.4, 4.2), 7.20(1H, t, J=6.9), about 7.6(2H, bs) |
| 6 | 3360, 3290, 1695, 1629, 1546, 1508, 1448, 1330, 1054 | (400MHz) 1.05(3H, t, J=7.5), 2.07(3H, s), 2.12(3H, s), 2.22(1H, dd, J=4.8, 1.9), 2.46(1H, d, J=4.8), 2.51 (2H, q, J=7.5), 3.13(2H, m), 3.66(1H, dd, J=12.9, 1.9), 3.73(2H, bq, J=6.7), 4.23(1H, dd, J=10.0, 3.4), 4.42(1H, d, J=12.9), 5.22(1H, t, J=10.3), 5.47(1H, dd, J=10.5, 3.4), 7.20(1H, t, J=6.5), 7.49(2H, bs), 8.34(1H, s). |
| 7 | 3280, 1716, 1683, 1628, 1547, 1506, 1440, 1321, | (400MHz) 1.82(2H, quint, J=7.0), 2.10(3H, s), 2.28(3H, s), 2.75(1H, dd, J=4.4, 2.0), 2.96(2H, t, |

TABLE 10-continued

| Compound | IR (cm$^{-1}$) | NMR (δ) |
|---|---|---|
|  | 1053 | J=7.1), 3.13(1H, d, J=4.4), 3.22(3H, s), 3.56(2H, q, J=6.5), 3.60(1H, dd, J=12.7, 2.0), 3.99(1H, dd, J=10.8, 4.4), 4.54(1H, d, J=12.7), 5.03(1H, t, J=10.7), 5.38(1H, dd, J=10.5, 4.4), 7.07(1H, t, J=6.2), 7.61(2H, bs). |
| 8 | 3440, 1690, 1629, 1545, 1511, 1465, 1450, 1332 | (400MHz) 1.77(2H, quint, J=7.1), 2.07(3H, s), 2.12 (3H, s), 2.23(1H, dd, J=4.8, 1.9), 2.27(3H, s), 2.47(1H, d, J=4.8), 2.91(2H, t, J=7.1), 3.49(2H, q, J=6.9), 3.68(1H, dd, J=12.9, 1.9), 4.24(1H, dd, J=10.0, 3.4), 4.46(1H, d, J=12.9), 5.23(1H, t, J=10.3), 5.48(1H, dd, J=10.5, 3.4), 7.08(1H, t, J=6.5), 7.50(2H, bs), 8.36(1H, bs). |
| 9 | 3270, 2900, 1710, 1677, 1620, 1540, 1500, 1434, 1319, 1050 | (100MHz) 1.56(4H, sm), 2.10(3H, s), 2.28(3H, s), 2.75 (1H, bs), 2.90(2H, t, J=6.8), 3.11(1H, bs), 3.22(3H, s), 3.46(2H, q, J=6.6), 3.60(1H, bd, J=12.7), 3.99 (1H, dd, J=10.8, 4.4), 4.55(1H, d, J=12.7), 5.06(1H, bt, J=10.6), 5.39(1H, dd, J=10.3, 4.4), 6.94(1H, t, J=6.6), 7.62(2H, bs). |
| 10 | 3280, 2920, 1715, 1683, 1628, 1548, 1507, 1440, 1320, 1051 | (100MHz) 1.2-1.7(6H, m), 2.12(3H, s), 2.29(3H, s), 2.76(1H, bs), 2.89(2H, t, J=7.1), 3.13(1H, bs), 3.22 (3H, s), 3.43(1H, q, J=6.4), 3.61(1H, bd, J=12.9), 4.00(1H, dd, J=10.8, 4.4), 4.57(1H, d, J=12.9), 5.07 (1H, dt, J=10.6), 5.40(1H, dd, J=10.3, 4.4), 6.91 (1H, dt, J=6.3), 7.62(2H, bs). |
| 11 | 3290, 2930, 1717, 1686, 1630, 1550, 1509, 1444, 1325, 1057 | (100MHz) 1.2-1.6(8H, m), 2.13(3H, s), 2.30(3H, s), 2.76(1H, bs), 2.89(2H, t, J=6.8), 3.15(1H, bd, J=4.4), 3.23(3H, s), 3.44(2H, q, J=6.8), 3.62(1H, dd, J=12.7, 2.0), 4.01(1H, dd, J=11.0, 4.4), 4.57 (1H, d, J=12.7), 5.06(1H, t, J=10.8), 5.40(1H, dd, J=10.5, 4.4), 6.94(1H, bt, J=6.8), 7.63(2H, bs). |
| 12 | 3300, 2930, 1720, 1688, 1631, 1555, 1510, 1445, 1322, 1053 | (400MHz) 1.1-1.3(8H, m), 1.47(2H, quint, J=7.2), 1.53(2H, quint, J=7.2), about 2.1(1H), 2.15(3H, s), 2.30(3H, s), 2.76(1H, bs), 2.92(2H, t, J=7.3), 3.15 (1H, bs), 3.23(3H, s), 3.46(2H, q, J=6.9), 3.62(1H, bd, J=12.7), 4.01(1H, dd, J=11.1, 4.2), 4.57(1H, d, J=12.7), about 5.1(1H), 5.40(1H, dd, J=10.4, 4.2), 6.96(1H, t, J=6.1), about 7.6(2H, bs). |

EXAMPLE 2

7-N-[2-(4-fluorobenzoylthio)ethyl]mitomycin D (Compound 19)

328 mg of TPP and 246 μl of DIAD were dissolved in anhydrous tetrahydrofuran (3.0 ml), and the solution were stirred for 30 minutes in argon atmosphere under cooling with ice water. To this solution was added 3.0 ml of anhydrous tetrahydrofuran which contained 189 mg of Compound b and 195 mg of 4-fluorothiobenzoic acid purified by sublimation. The mixture was stirred for 5 minutes under ice-cooling, diluted with ethyl acetate (50 ml) and washed with a saturated aqueous solution of sodium bicarbonate. After removing the ethyl acetate layer, the sodium bicarbonate solution layer was extracted twice with ethyl acetate. The ethyl acetate layers were combined, washed six times with 50 ml of a saturated aqueous solution of sodium bicarbonate and once with a saturated aqueous sodium chloride solution, and then dried over anhydrous sodium sulfate. The drying agent was removed by filtration, followed by evaporating the solvent under reduced pressure. The residue was chromatographed using a column packed with silica gel (75 g). Elution was effected with chloroform/methanol 93:7). Blue fractions which showed an Rf value of 0.33 by TLC using chloroform/methanol (9:1) were collected and combined. The solvent was evaporated under reduced pressure. The residue was dissolved in a small amount of chloroform and powderized with n-hexane. The solvent was evaporated under reduced pressure. The residue was held at room temperature under reduced pressure to remove the solvent adequately, whereby Compound 19 (213 mg; 82.5%) was obtained as grayish green powder.

Starting material, reagent, appearance, yield, M.P. and MS of Compound 19 and Compounds 13–18 and 20–25 synthesized in the same manner as described above are shown in Table 11, and IR and NMR of these compounds in Table 12.

TABLE 11

Synthesis and physical properties of typical Compounds (I)

| Starting materials and reagents | Product | Appearance | Yield (%) | M.P. (°C.) | MS (SI) | M. formula M. weight |
|---|---|---|---|---|---|---|
| C No. a (284 mg) TB (221 μl) TPP (492 mg), DIAD (369 μl) | C No. 13 | Grayish blue powder | 82.0 | 98 | m/z 501 (M$^+$ + 3) | $C_{24}H_{26}N_4O_6S$ 498 |
| C No. b (200 mg) TB (156 μl) TPP (348 mg), DIAD (261 μl) | C No. 14 | Grayish green powder | 92.6 | 110–112 | m/z 500 (M$^+$ + 2) | $C_{24}H_{26}N_4O_6S$ 498 |
| C No. d (127 mg) TB (94 μl) TPP (210 mg), DIAD (158 μl) | C No. 15 | Dark brown powder | 61.7 | 96 | m/z 440 (M$^+$ + 3) | $C_{23}H_{23}N_3O_4S$ 437 |
| C No. c (158 mg) | C No. 16 | Dark | 85.7 | 88 | m/z 515 | $C_{25}H_{28}N_4O_6S$ |

TABLE 11-continued

Synthesis and physical properties of typical Compounds (I)

| Starting materials and reagents | Product | Appearance | Yield (%) | M.P. (°C.) | MS (SI) | M. formula M. weight |
|---|---|---|---|---|---|---|
| TB (94 μl) TPP (210 mg), DIAD (158 μl) | | blue solid | | | ($M^+ + 3$) | 512 |
| C No. j (217 mg) TB (147 μl) TPP (328 mg), DIAD (246 μl) | C No. 17 | Dark blue solid | 81.6 | 70 | m/z 556 ($M^+ + 2$) | $C_{28}H_{34}N_4O_6S$ 554 |
| C No. a (189 mg) 4-FTB (156 mg) TPP (262 mg), DIAD (197 μl) | C No. 18 | Grayish blue powder | 48.5 | 104 | m/z 518 ($M^+ + 2$) | $C_{24}H_{25}FN_4O_6S$ 516 |
| C No. b (189 mg) 4-FTB (195 mg) TPP (328 mg), DIAD (246 μl) | C No. 19 | Grayish green powder | 82.5 | 106–109 | m/z 518 ($M^+ + 2$) | $C_{24}H_{25}FN_4O_6S$ 516 |
| C No. k (163 mg) 4-FTB (110 mg) TPP (185 mg), DIAD (139 μl) | C No. 20 | Dark blue solid | 62.2 | 51 | m/z 603 ($M^+ + 3$) | $C_{30}H_{37}FN_4O_6S$ 600 |
| C No. a (284 mg) 4-BTB (407 mg) TPP (492 mg), DIAD (369 μl) | C No. 21 | Grayish blue powder | 72.3 | 105 | m/z 581 ($M^+ + 3$, $C_{24}H_{25}{}^{81}BrN_4O_6S$) | $C_{24}H_{25}BrN_4O_6S$ 577 |
| C No. b (189 mg) 4-BTB (271 mg) TPP (328 mg), DIAD (246 μl) | C No. 22 | Grayish green powder | 74.3 | 116 | m/z 581 ($M^+ + 3$, $C_{24}H_{25}{}^{81}BrN_4O_6S$) | $C_{24}H_{25}BrN_4O_6S$ 577 |
| C No. a (189 mg) 4-MTB (210 mg) TPP (328 mg), DIAD (246 μl) | C No. 23 | Grayish blue powder | 69.2 | 98 | m/z 531 ($M^+ + 3$) | $C_{25}H_{28}N_4O_7S$ 528 |
| C No. b (95 mg) 4-MTB (105 mg) TPP (164 mg), DIAD (123 μl) | C No. 24 | Grayish green powder | 86.9 | 114 | m/z 531 ($M^+ + 3$) | $C_{25}H_{28}N_4O_7S$ 528 |
| C No. b (95 mg) 4-NTB (94 mg) TPP (164 mg), DIAD (123 μl) | C No. 25 | Grayish green powder | 61.2 | 118–120 | m/z 545 ($M^+ + 2$) | $C_{24}H_{25}N_5O_8S$ 543 |

TB ... Thiobenzoic acid, 4-FTB ... 4-fluoro-thiobenzoic acid, 4-BTB ... 4-bromo-thiobenzoic acid, 4-MTB ... 4 methoxy-thiobenzoic acid 4-NTB ... 4-nitro-thiobenzoic acid

TABLE 12

IR and NMR data of typical Compounds (I)

| Compound | IR (cm$^{-1}$) | NMR (δ) |
|---|---|---|
| 13 | 3300, 1720, 1632, 1558, 1510, 1447, 1324, 1203, 1060, 909, 687 | (400MHz) 2.10(1H, bt, J=6.7), 2.16(3H, s), 2.74(1H, bs), 3.14(1H, bs), 3.22(3H, s), 3.41(2H, m), 3.59(1H, bd, J=12.7), 3.91(2H, m), 3.99(1H, dd, J=11.2, 4.2), 4.52(1H, d, J=12.7), 5.10(1H, bt, J=10.7), 5.39(1H, dd, J=10.4, 4.2), 7.32(1H, t, J=6.7), 7.40(2H, bt, J=7.4), 7.51(2H, bt, J=7.4), ~7.6(2H, bs), 8.06(2H, bd, J=7.1) |
| 14 | 3280, 1710, 1630, 1547, 1510, 1445, 1328, 1202, 909, 687 | (100MHz) 2.11(3H, s), 2.12(3H, s), 2.22(1H, dd, J=4.6, 1.7), 2.46(1H, d, J=4.6), 3.33(2H, t, J=6.5), 3.66(1H, dd, J=12.9, 1.7), 3.85(2H, q, J=6.5), 4.22(1H, dd, J=9.8, 3.7), 4.43(1H, d, J=12.9), 5.21(1H, t, J=10.2), 5.48(1H, dd, J=10.5, 3.7), ~7.2(1H), 7.3–7.6(3H, m), ~7.5(2H), ~8.1(2H, m), 8.35(1H, bs) |
| 15 | 3280, 1662, 1640, 1508, 1443, 1201, 1047, 906, 686 | (400MHz) 2.09(3H, s), 2.15(3H, s), 2.28(1H, dd, J=4.7, 1.8), 2.62(1H, d, J=4.7), 3.33(2H, bt, J=6.8), 3.74(1H, dd, J=12.8, 1.8), 3.84(2H, q, J=6.7), 4.7(1H, d, J=12.8), 5.81(1H, d, J=1.2), 6.49(1H, d, J=1.2), 7.36(1H, t, J=6.6), 7.40(2H, bt, J=7.7), 7.53(1H, bt, J=7.4), 8.04(2H, bd, J=8.4), ~8.7(1H, bs) |
| 16 | 3290, 1720, 1660, 1630, 1558, 1506, 1442, 1319, 1201, 1053, 905, 683 | (400MHz) 2.15(1H, dd, J=4.6, 2.1), 2.17(3H, s), 2.24(3H, s), 2.54(1H, d, J=4.6), 3.18(3H, s), 3.41(2H, bt, J=6.8), 3.52(1H, dd, J=12.8, 2.1), 3.92(2H, m), 3.95(1H, dd, J=11.3, 4.4), 4.44(1H, d, J=12.8), 4.79(1H, dd, J=11.3, 10.4), 5.31(1H, dd, J=10.4, 4.4), 7.35(1H, t, J=6.5), 7.41(2H, bt, J=7.6), 7.52(1H, tt, J=7.4, 1.8), ~7.6(2H, bs), 8.06(2H, bd, J=8.4) |
| 17 | 3300, 2930, 1720, 1659, 1631, 1551, 1510, 1444, 1323, 1200, 1055, 910, 687 | (400MHz) 1.2–1.4(4H, m), 1.47(2H, quint, J=7.3), 1.61(2H, quint, J=7.3), 2.10(1H, bt, J=7.6), 2.14(3H, s), 2.75(1H, bs), 3.11(2H, t, J=7.3), 3.15(1H, m), 3.22(3H, s), 3.45(2H, q, J=6.9), 3.60(1H, bd, J=12.7), 4.01(1H, dd, J=11.2, 4.2), 4.57(1H, d, J=12.7), 5.10(1H, bt, J=10.8), 5.40(1H, dd, J=10.4, 4.2), 6.94(1H, bt, J=6.2), 7.43(2H, bt, J=7.8), 7.53(1H, tt, J=7.4, 1.3), ~7.6(2H, bs), 8.13(2H, bd, J=8.3) |
| 18 | 3300, 1720, 1661, 1634, 1600, 1560, 1505, 1450, 1327, 1226, 1204, 1062, 917, 847, 621 | (400MHz) 2.10(1H, bs), 2.16(3H, s), 2.77(1H, bs), 3.17(1H, bs), 3.22(3H, s), 3.42(2H, m), 3.59(1H, bd, J=12.7), 3.93(2H, m), 3.98(1H, dd, J=11.2, 4.3), 4.50(1H, d, J=12.7), ~5.2(1H, t), 5.36(1H, dd, J=10.4, 4.3), 7.21(2H, t, J=8.9), 7.33(1H, t, J=6.4), ~7.6(2H, bs), 8.07(2H, dd, J=9.0, 5.4) |

TABLE 12-continued

IR and NMR data of typical Compounds (I)

| Compound | IR (cm$^{-1}$) | NMR ($\delta$) |
|---|---|---|
| 19 | 3280, 1708, 1657, 1629, 1594, 1545, 1507, 1447, 1328, 1221, 1200, 1151, 911, 841, 617 | (400MHz) 2.11(3H, s), 2.12(3H, s), 2.23(1H, dd, J=4.7, 1.9), 2.47(1H, d, J=4.7), 3.34(2H, m), 3.67(1H, d, J=12.9, 1.9), 3.85(2H, q, J=6.8), 4.23(1H, dd, J=10.0, 3.4), 4.42(1H, d, J=12.9), 5.22(1H, t, J=10.3), 5.47 (1H, dd, J=10.5, 3.4), 7.19(2H, t, J=8.8), 7.31(1H, t, J=6.6), 7.48(2H, bs), 8.05(2H, dd, J=9.0, 5.4), 8.34(1H, bs) |
| 20 | 3290, 2920, 1718, 1656, 1594, 1554, 1499, 1440, 1320, 1194, 1052, 910, 837, 613 | (400MHz) 1.22(6H, bs), 1.34(2H, m), 1.49(2H, b.quint, J=7.1), 1.64(2H, quint, J=7.4), 2.10(1H, bs), 2.15 (3H, s), 2.76(1H, bs), 3.13(2H, t, J=7.4), ~3.15(1H), 3.22(3H, s), 3.47(2H, q, J=6.9), 3.61(1H, bd, J=12.7), 4.01(1H, dd, J=11.1, 4.2), 4.57(1H, d, J=12.7), 5.09 (1H, bt, J=10.8), 5.39(1H, dd, J=10.4, 4.2), 6.96(1H, t, J=6.2), 7.21(2H, t, J=8.7), ~7.6(2H, bs), 8.13(2H, dd, J=8.8, 5.3) |
| 21 | 3300, 1718, 1663, 1631, 1560, 1510, 1449, 1327, 1206, 1066, 911 | (400MHz) 2.10(1H, bs), 2.15(3H, s), 2.75(1H, bs), 3.14(1H, bs), 3.22(3H, s), 3.40(2H, m), 3.59(1H, bd, J=12.7), 3.91(2H, m), 3.99(1H, dd, J=11.2, 4.2), 4.51 (1H, d, J=12.7), 5.09(1H, bt, J=10.9), 5.38(1H, dd, J=10.4, 4.2), 7.32(1H, t, J=6.6), ~7.6(2H, bs), 7.63 (2H, d, J=8.5), 7.90(2H, d, J=8.5) |
| 22 | 3290, 1706, 1659, 1629, 1547, 1510, 1448, 1328, 1203, 1064, 908 | (400MHz) 2.11(3H, s), 2.12(3H, s), 2.23(1H, dd, J=4.7, 1.9), 2.46(1H, d, J=4.7), 3.34(2H, m), 3.67(1H, dd, J=12.9, 1.9), 3.85(2H, q, J=6.8), 4.23(1H, dd, J=10.0, 3.4), 4.42(1H, d, J=12.9), 5.22(1H, t, J=10.3), 5.47 (1H, dd, J=10.5, 3.4), 7.31(1H, t, J=6.6), 7.47(2H, bs), 7.63(2H, d, J=8.5), 7.88(2H, d, J=8.5), 8.34(1H, bs) |
| 23 | 3270, 1710, 1622, 1590, 1547, 1499, 1438, 1313, 1249, 1203, 1155, 1050, 900 | (400MHz) 2.09(1H, bs), 2.16(3H, s), 2.75(1H, bs), 3.14(1H, bs), 3.21(3H, s), 3.41(2H, m), 3.59(1H, bd, J=12.7), 3.69(3H, s), 3.91(2H, m), 3.99(1H, dd, J=11.2, 4.2), 4.52(1H, d, J=12.7), 5.09(1H, bt, J=10.8), 5.38(1H, dd, J=10.4, 4.2), 7.00(2H, d, J=9.0), 7.32 (1H, t, J=6.7), ~7.6(2H, bs), 8.10(2H, d, J=9.0) |
| 24 | 3370, 3300, 1710, 1632, 1602, 1552, 1510, 1451, 1329, 1260, 1213, 1067, 911 | (400MHz) 2.12(3H×2, s), 2.22(1H, dd, J=4.7, 1.9), 2.46 (1H, d, J=4.7), 3.34(2H, m), 3.67(1H, dd, J=12.9, 1.9), 3.69(3H, s), 3.85(2H, q, J=6.9), 4.23(1H, dd, J=10.1, 3.4), 4.42(1H, d, J=12.9), 5.22(1H, t, J=10.3), 5.47 (1H, dd, J=10.5, 3.4), 6.99(2H, d, J=9.0), 7.32(1H, t, J=6.7), 7.48(2H, bs), 8.08(2H, d, J=9.0), 8.33(1H, bs) |
| 25 | 3380, 3300, 1711, 1668, 1634, 1608, 1554, 1520, 1453, 1415, 1350, 1330, 1204, 1111, 1059, 923, 852, 697 | (400MHz) 2.11(3H, s), 2.13(3H, s), 2.24(1H, dd, J=4.7, 1.9), 2.48(1H, d, J=4.7), 3.40(2H, m), 3.68(1H, dd, J=12.9, 1.9), 3.89(2H, q, J=6.8), 4.23(1H, dd, J=10.1, 3.4), 4.42(1H, d, J=12.9), 5.21(1H, t, J=10.3), 5.46 (1H, dd, J=10.5, 3.4), 7.33(1H, t, J=6.8), 7.49(2H, bs), 8.12(2H, d, J=8.9), 8.30(2H, d, J=8.9), 8.36(1H, bs) |

EXAMPLE 3

7-N-(2-dithioacetyloxyethyl)mitomycin D (Compound 27)

328 mg of TPP and 246 μl of DIAD were dissolved in anhydrous tetrahydrofuran (3 ml). The solution was stirred for 40 minutes in argon atmosphere under cooling with ice water. To the solution was added a solution of Compound b (189 mg) and dithioacetic acid (93 μl) in tetrahydrofuran (5 ml). After stirring the mixture for 30 minutes under ice-cooling, the reaction solution was diluted with ethyl acetate (50 ml) and washed with a saturated aqueous solution of sodium bicarbonate. After removal of the ethyl acetate layer, the sodium bicarbonate solution layer was extracted three times with 50 ml of ethyl acetate. The ethyl acetate layers were combined together, washed with a saturated aqueous solution of sodium bicarbonate (50 ml) and with a saturated aqueous solution of sodium chloride, and dried over anhydrous sodium sulfate. The drying agent was removed by filtration, and the solvent was removed by evaporation under reduced pressure. The residue was chromatographed using a column packed with silica gel (75 g). Elution was effected with chloroform/methanol (95:5). Blue fractions which showed an Rf value of 0.37 by TLC chloroform/methanol (9:1) were collected and combined. After removal of the solvent by evaporation under reduced pressure, the residue was chromatographed using a column packed with silica gel (50 g). Elution was effected with chloroform/acetone/methanol (70:25:5). Blue fractions which showed an Rf value of 0.26 by TLC using the same solvent system as above were collected and combined. After removing the solvent by evaporation under reduced pressure, the residue was dissolved in a small amount of chloroform and powderized with n-hexane. The solvent was evaporated off under reduced pressure, and the residue was dried at 35° C. overnight under reduced pressure to obtain Compound 27 (155 mg; 68.7%) as grayish green powder.

Starting material, reagent, appearance, yield, M.P. and MS of Compound 27 and Compounds 26 and 28–31 synthesized in the same manner as described above are shown in Table 13, and IR and NMR of these compounds in Table 14.

TABLE 13

Synthesis and physical properties of typical Compounds (I)

| Starting materials and reagents | Product | Appearance | Yield (%) | M.P. (°C.) | M S | M. formula M. weight |
|---|---|---|---|---|---|---|
| C No. a (189 mg) DTA (93 μl) TPP (328 mg), DIAD (246 μl) | C No. 26 | Dark bluish purple powder | 68.7 | 82–83 | (SI) m/z 454 ($M^+ + 2$) | $C_{19}H_{24}N_4O_5S_2$ 452 |
| C No. b (189 mg) DTA (93 μl) TPP (328 mg), DIAD (246 μl) | C No. 27 | Grayish green powder | 68.7 | 89–93 | (SI) m/z 454 ($M^+ + 2$) | $C_{19}H_{24}N_4O_5S_2$ 452 |
| C No. c (196 mg) DTA (93 μl) TPP (328 mg), DIAD (246 μl) | C No. 28 | Dark blue power | 85.8 | 67–71 | (EI) m/z 467 ($M^+ + 1$) | $C_{20}H_{26}N_4O_5S_2$ 466 |
| C No. d (159 mg) DTA (93 μl) TPP (328 mg), DIAD (246 μl) | C No. 29 | Dark greenish brown powder | 42.5 | 84–88 | (EI) m/z 392 ($M^+ + 1$) | $C_{18}H_{21}N_3O_3S_2$ 391 |
| C No. h (203 mg) DTA (93 μl) TPP (328 mg), DIAD (246 μl) | C No. 30 | Dark bluish purple powder | 53.1 | 78–81 | (EI) m/z 480 ($M^+$) | $C_{21}H_{28}N_4O_5S_2$ 480 |
| C No. j (217 mg) DTA (93 μl) TPP (328 mg), DIAD (246 μl) | C No. 31 | Dark bluish purple powder | 69.3 | 59–63 | (EI) m/z 508 ($M^+$) | $C_{23}H_{32}N_4O_5S_2$ 508 |

DTA . . . dithioacetic acid; M. formula . . . Molecular formula; M. weight . . . Molecular weight

TABLE 14

IR and NMR data of typical Compounds (I)

| Compound | IR (cm$^{-1}$) | N M R (δ) (400MHz, CDCl$_3$) |
|---|---|---|
| 26 | 3300, 1714, 1633, 1557, 1511, 1450, 1329, 1193, 1063, 862 | ~0.8(1H, bs), 1.98(3H, s), 2.82(1H, dd, J=4.5, 1.9), 2.85(3H, s), 2.90(1H, d, J=4.5), 3.21(3H, s), 3.46 (2H, t, J=6.6), 3.51(1H, dd, J=12.9, 1.9), 3.60(1H, dd, J=10.5, 4.4), 3.82(2H, q, J=6.6), 4.26(1H, d, J=12.9), 4.49(1H, t, J=10.6), 4.70(1H, dd, J=10.7, 4.4), 4.81(2H, bs), 6.34(1H, bt, J=6.5) |
| 27 | 3350, 3280, 1704, 1629, 1548, 1509, 1448, 1329, 1192, 1109, 1054, 860 | 1.95(3H, s), 2.24(1H, d, J=4.7), 2.27(3H, s), 2.28 (1H, dd, J=4.7, 1.9), 2.85(3H, s), 3.45(2H, m), 3.51 (1H, dd, J=13.0, 1.9), 3.70(1H, t, J=4.7), 3.81(2H, q, J=6.6), 4.13(1H, d, J=13.0), 4.46(1H, bs), 4.70 (2H, d, J=4.7), 4.82(2H, bs), 6.36(1H, t, J=6.5) |
| 28 | 3290, 2950, 1720, 1632, 1560, 1509, 1448, 1321, 1191, 1106, 1057, 861 | 1.98(3H, s), 2.24(1H, dd, J=4.7, 2.0), 2.26(3H, s), 2.28(1H, d, J=4.7), 2.85(3H, s), 3.18(3H, s), 3.46 (2H, t, J=6.6), 3.46(1H, dd, J=12.9, 2.0), 3.57(1H, dd, J=10.9, 4.4), 3.82(2H, q, J=6.6), 4.22(1H, d, J=12.9), 4.35(1H, t, J=10.7), 4.69(1H, dd, J=10.6, 4.4), 4.74(2H, bs), 6.34(1H, t, J=6.2) |
| 29 | 3250, 1634, 1528, 1503, 1438, 1190, 1042, 854 | 1.87(3H, s), 2.20(3H, s), 2.23(1H, dd, J=4.7, 1.9), 2.28(1H, d, J=4.7), 2.86(3H, s), 3.45(2H, t, J=6.7), 3.50(1H, dd, J=12.9, 1.9), 3.80(2H, m), 4.16(1H, d, J=12.9), 4.26(1H, bs), 5.49(1H, s), 5.98(1H, s), 6.42(1H, bt, J=6.3) |
| 30 | 3280, 2920, 1716, 1629, 1550, 1508, 1441, 1321, 1186, 1052, 857 | ~0.7(1H, bs), ~1.73(4H, m), 2.01(3H, s), ~2.8(1H), 2.83(3H, s), 2.89(1H, bd, J=3.6), 3.21(3H, s), 3.24 (2H, t, J=7.0), 3.52(1H, bd, J=12.9), 3.56(2H, q, J=6.4), 3.60(1H, dd, J=10.6, 4.3), 4.29(1H, d, J= 12.9), 4.50(1H, bt, J=10.3), 4.70(1H, dd, J=10.7, 4.3), 4.73(2H, bs), 6.30(1H, bt, J=5.7) |
| 31 | 3290, 2925, 1717, 1630, 1550, 1508, 1441, 1323, 1187, 1054, 858 | ~0.7(1H, bs), 1.49(4H, m), 1.61(2H, quint, J=7.3), 1.69(2H, quint, J=7.4), 2.02(3H, s), ~2.8(1H), 2.83 (3H, s), 2.89(1H, bd, J=4.3), 3.21(3H, s), 3.21(2H, t, J=7.4), ~3.5(1H), 3.53(2H, q, J=6.9), 3.60(1H, dd, J=10.5, 4.4), 4.30(1H, d, J=12.9), 4.50(1H, bt, J= 10.4), 4.70(1H, dd, J=10.8, 4.4), 4.74(2H, bs), 6.33 (1H, bt, J=5.8) |

EXAMPLE 4

7-N-(3-acetylthiopropyl)mitomycin D (Compound 8)

(Another process)

33.0 mg of Compound p was dissolved in anhydrous dimethylsulfoxide (1 ml), and the solution was stirred in argon atmosphere at room temperature. Then, 40.1 mg of potassium thioacetate was added thereto and the mixture was stirred for one hour. The reaction solution was diluted with chloroform (30 ml) and washed with a saturated aqueous solution of sodium bicarbonate. After removal of the chloroform layer, the sodium bicarbonate solution layer was twice extracted with 30 ml of chloroform. The chloroform layers were combined together, washed with a saturated aqueous solution of sodium bicarbonate and with a saturated aqueous solution of sodium chloride, and dried over anhydrous sodium sulfate. After removal of the drying agent by filtration, solvent was evaporated off under reduced pressure. The residue was subjected to silica gel thin layer chromatography [developing solvent, chloroform/methanol (9:1)], and the blue part exhibiting an Rf value of 0.42 was scraped and eluted using the same solvent system. After the solvent was removed by evaporation under reduced pressure, the residue was dissolved in a small amount of chloroform and powderized with n-hexane. The solvent was evaporated off under reduced pressure and the residue was held at room temperature under reduced pressure to remove the solvent adequately, whereby Compound 8 (24.8 mg, 78.5%) was obtained as grayish green powder.

Appearance, M.P., MS, IR and NMR of Compound 8 and Compounds 1, 7, 17, 18, 21, 24 and 25 synthesized in the same manner as described above substantially accorded with those exhibited in Tables 9, 10, 11 and 12. Starting material, reagent and yield of these compounds are shown in Table 15.

TABLE 15

| Starting materials and reagents | Product | Yield (%) |
|---|---|---|
| C No. 1 (22.1 mg) PTA (28.6 mg) | C No. 1 | 46.8 |
| C No. n (84.9 mg) PTA (118.1 mg) | C No. 7 | 36.8 |
| C No. p (33.0 mg) PTA (40.1 mg) | C No. 8 | 78.5 |
| C No. q (68.5 mg) PTB (102.5 mg) | C No. 17 | 67.5 |
| C No. m (40.0 mg) P-4-FTB (48.6 mg) | C No. 18 | 68.4 |
| C No. m (40.0 mg) P-4-BTB (63.8 mg) | C No. 21 | 72.3 |
| C No. o (40.0 mg) P-4-MTB (51.6 mg) | C No. 24 | 77.7 |
| C No. o (40.0 mg) P-4-NTB (55.3 mg) | C No. 25 | 69.2 |

PTA ... Potassium thioacetate,
PTB ... Potassium thiobenzoate,
P-4-FTB ... Potassium 4-fluorothiobenzoate
P-4-BTB ... Potassium 4-bromothiobenzoate
P-4-MTB ... Potassium 4-methoxythiobenzoate
P-4-NTB ... Potassium 4-nitrothiobenzoate

EXAMPLE 5

Injection

Compound 1 (20 g) and purified mannitol (40 g) are dissolved in water for injection to make the volume of 20 l. After the solution is aseptically filtered, 5 ml portions of the solution are put into brown vials and freeze-dried in a conventional manner to obtain freeze-dried preparations of 5 mg/vial.

EXAMPLE 6

Tablet

Lactose (400 g), calcium carbonate (1200 g) and carboxymethylcellulose calcium (300 g) are mixed, and 16% aqueous hydroxypropylmethylcellulose (500 g) is added thereto. The mixture is kneaded, granulated and dried in a conventional manner to prepare granules. The granules are mixed with addition of Compound 18 (10 g) and then with addition of magnesium stearate (10 g). The mixture is compressed with a tableting machine having a punch (diameter: 8 mm) (Model RT-15, Kikusui Seisakusho Co.) to obtain tablets (200 mg/tablet). The tablet contains 1 mg of Compound 18 per tablet.

EXAMPLE 7

Tablet

Compound 26 (50 g), crystalline cellulose (170 g), lower-substituted hydroxypropylcellulose (17 g) and magnesium stearate (3 g) are mixed in a 1 l-V-type blender. The mixture is compressed with a tableting machine having a punch (diameter: 9 mm) (Model RT-15 rotary type, Kikusui Seisakusho Co.) to obtain tablets (240 mg/tablet). The tablet contains 50 mg of Compound 26 per tablet.

REFERENCE EXAMPLE 1

7-N-(3-hydroxypropyl)mitomycin D (Compound g)

524 mg of mitomycin B was dissolved in methanol (5 ml) and 3-amino-1propanol (126.2 μl) was added to the solution. The mixture was stirred at room temperature for 2 hours and 40 minutes. The solvent was removed by evaporation under reduced pressure and the residue was chromatographed over silica gel (60 g) in a column. Elution was effected with chloroform/methanol (9:1) and the fractions exhibiting an Rf value of 0.19 in TLC developed with the same solvent as above were collected and combined. The solvent was evaporated off under reduced pressure. The residue was dissolved in a small amount of a mixed solvent of acetone and chloroform, and powderized with n-hexane. The solvent was evaporated off under reduced pressure and the resulting powder was heated at 50° C. for 3 hours under reduced pressure to obtain Compoung g (576.2 mg, 98.0%) as dark blue powder.

Starting material, yield, M.P. and MS of Compound g and Compounds a–f and h–k synthesized in the same manner as described above are shown in Table 16, and IR and NMR of these compounds in Table 17.

TABLE 16

Synthesis and physical properties of typical Compounds (II)

| Compound | Starting materials | | Yield (%) | M.P. (°C.) | MS (EI) M+(m/z) | M. formula and M. weight | |
|---|---|---|---|---|---|---|---|
| | Mitomycin | Amine | | | | | |
| g | mitomycin B | HO(CH$_2$)$_3$NH$_2$ | 98.0 | 101.0–113.0 | 392 | C$_{18}$H$_{24}$N$_4$O$_6$ | 392 |
| b | mitomycin B | HO(CH$_2$)$_2$NH$_2$ | 99.0 | 114.0–121.0 | 378 | C$_{17}$H$_{22}$N$_4$O$_6$ | 378 |
| c | mitomycin F | HO(CH$_2$)$_2$NH$_2$ | 99.0 | 94.5–103.0 | 392 | C$_{18}$H$_{24}$N$_4$O$_6$ | 392 |
| d | mitomycin H | HO(CH$_2$)$_2$NH$_2$ | 94.6 | 173.0–174.5 | 317 | C$_{16}$H$_{19}$N$_3$O$_4$ | 317 |
| h | mitomycin A | HO(CH$_2$)$_4$NH$_2$ | 93.2 | 73.0–81.5* | 406 | C$_{19}$H$_{26}$N$_4$O$_6$ | 406 |
| i | mitomycin A | HO(CH$_2$)$_5$NH$_2$ | 98.1 | 65.0–73.0 | 420 | C$_{20}$H$_{28}$N$_4$O$_6$ | 420 |
| j | mitomycin A | HO(CH$_2$)$_6$NH$_2$ | 91.7 | 64.5–70.5 | 434 | C$_{21}$H$_{30}$N$_4$O$_6$ | 434 |
| k | mitomycin A | HO(CH$_2$)$_8$NH$_2$ | 76.6 | 59.0–63.0 | 462 | C$_{23}$H$_{34}$N$_4$O$_6$ | 462 |

*Decomposed.

TABLE 17

IR and NMR data of typical Compounds (II)

| Compound | IR (cm$^{-1}$) | NMR ($\delta$) |
|---|---|---|
| g | 3290, 1708, 1630, 1510, 1467, 1450, 1414, 1332, 1054 | (400MHz) 1.85(2H, quint, J=6.3), 2.11(3H, s), 2.12 (3H, s), 2.22(1H, dd, J=4.8, 1.9), 2.46(1H, d, J=4.8), 3.68(1H, dd, J=12.9, 1.9), 3.73(2H, q, J=6.6), 3.87 (2H, bs), 4.22(1H, dd, J=10.1, 3.4), 4.66(1H, d, J= 12.9), 5.21(1H, t, J=10.3), 5.49(1H, dd, J=10.5, 3.4), 6.35(1H, bs), 7.33(1H, t, J=6.0), 7.50(2H, bs), 8.33(1H, s) |
| b | 3290, 1709, 1630, 1594, 1512, 1450, 1333, 1059 | (400MHz) 2.10(3H, s), 2.13(3H, s), 2.22(1H, dd, J=4.8, 1.9), 2.46(1H, d, J=4.8), 3.67(1H, dd, J=12.9, 1.9), 3.73(2H, q, J=5.6), 3.91(2H, bs), 4.21(1H, dd, J= 10.1, 3.5), 4.45(1H, d, J=12.9), 5.20(1H, t, J=10.3), 5.47(1H, dd, J=10.5, 3.5), 6.84(1H, bs), 7.41(1H, t, J=5.9), 7.47(2H, bs), 8.33(1H, s) |
| c | 3440, 3300, 1709, 1631, 1600, 1550, 1509, 1447, 1324, 1210, 1106, 1057 | (400MHz) 2.15(1H, dd, J=4.7, 2.1), 2.16(3H, s), 2.24 (3H, s), 2.53(1H, d, J=4.7), 3.18(3H, s), 3.52(1H, dd, J=12.9, 2.1), 3.80(2H, m), 3.93(1H, dd, J=11.3, 4.3), 3.97(2H, bs), 4.47(1H, d, J=12.9), 4.76(1H, dd, J=11.3, 10.5), 5.29(1H, dd, J=10.5, 4.3), 6.90 (1H, bs), 7.42(1H, t, J=6.0), about 7.6(2H, bs) |
| d | 3305, 1640, 1595, 1529, 1442, 1330, 1209, 1111, 1051 | (100MHz) 2.07(3H, s), 2.15(3H, s), 2.27(1H, dd, J= 4.9, 1.7), 2.62(1H, d, J=4.9), 3.71(2H, q, J=6.1), about 3.8(1H, m), 3.82(2H, m), 4.75(1H, d, J=12.9), 5.80(1H, d, J=1.3), 6.47(1H, d, J=1.3), 6.82(1H, bs), 7.42(1H, t, J=6.1), 8.87(1H, bs) |
| h | 3300, 1717, 1631, 1550, 1511, 1448, 1328, 1058 | (400MHz) 1.74(4H, m), 2.10(1H, bs), 2.13(3H, s), 2.75 (1H, bs), 3.15(1H, m), 3.22(3H, s), 3.57(2H, q, J= 6.8), 3.60(1H, bd, J=12.7), 3.84(2H, bs), 4.00(1H, dd, J=11.2, 4.2), 4.57(1H, d, J=12.7), 5.09(1H, t, J=10.8), 5.40(1H, dd, J=10.4, 4.2), 6.08(1H, bs), 7.06(1H, t, J=6.1), about 7.6(2H, bs) |
| i | 3430, 3290, 2930, 1715, 1630, 1550, 1510, 1446, 1328, 1058 | (400MHz) 1.54(4H, m), 1.70(2H, quint, J=6.7), 2.11 (1H, bs), 2.12(3H, s), 2.75(1H, bs), 3.15(1H, m), 3.22(3H, s), 3.47(2H, q, J=6.6), 3.60(1H, d, J= 12.7), 3.83(2H, bt, J=6.1), 4.00(1H, dd, J=11.2, 4.2), 4.57(1H, d, J=12.7), 5.09(1H, t, J=10.7), 5.40 (1H, dd, J=10.4, 4.2), 5.93(1H, bs), 6.94(1H, t, J=6.1), about 7.6(2H, bs) |
| j | 3430, 3300, 2930, 1716, 1631, 1550, 1510, 1447, 1328, 1059 | (400MHz) 1.34(2H, quint, J=6.9), 1.49(4H, m), 1.70 (2H, quint, J=7.0), 2.11(1H, bs), 2.13(3H, s), 2.75 (1H, bs), 3.15(1H, m), 3.22(3H, s), 3.45(2H, q, J= 6.8), 3.60(1H, bd, J=12.7), 3.85(2H, bt, J=6.2), 4.01(1H, dd, J=11.2, 4.2), 4.57(1H, d, J=12.7), 5.10(1H, t, J=10.7), 5.40(1H, dd, J=10.4, 4.2), 5.86(1H, bs), 6.93(1H, t, J=6.2), about 7.6(2H, bs) |
| k | 3420, 3290, 2920, 1710, 1630, 1549, 1509, 1445, 1323, 1054 | (400MHz) 1.25(6H, m), 1.47(4H, m), 1.73(2H, quint, J=7.1), 2.11(1H, bs), 2.15(3H, s), 2.76(1H, bs), 3.15(1H, m), 3.23(3H, s), 3.45(2H, q, J=6.9), 3.61 (1H, bd, J=12.7), 3.87(2H, bt, J=6.4), 4.01(1H, dd, J=11.2, 4.2), 4.57(1H, d, J=12.7), 5.09(1H, bt, J= 10.7), 5.40(1H, dd, J=10.4, 4.2), 5.86(1H, bs), 6.95(1H, bt, J=6.1), about 7.6(2H, bs) |

REFERENCE EXAMPLE 2

7-N-(2-chloroethyl)mitomycin D (Compound o)

698 mg of mitomycin B was dissolved in methanol (5 ml) and triethylamine (420 μl) was added to the solution. 290 mg of 2-chloroethylamine hydrochloride was added thereto, and the mixture was stirred at room temperature for 3 hours and allowed to stand overnight in a refrigerator. The reaction solution was diluted with chloroform (100 ml) and poured in a saturated aqueous solution of sodium bicarbonate. The chloroform layer was removed, and the sodium bicarbonate solution layer was extracted with chloroform (100 ml). The chloroform layer was washed with a saturated aqueous solution of sodium bicarbonate and with a saturated aqueous sodium chloride solution, and dried over anhydrous sodium sulfate. After the drying agent was removed by filtration, the solvent was evaporated off under reduced pressure. The residue was chromatographed over silica gel (150 g) in a column and eluted with chloroform/methanol (96:4). The blue fractions exhibiting an Rf value of 0.31 in TLC using chloroform/methanol (9:1) were combined. After the solvent was evaporated off under reduced pressure, the residue was dissolved in a small amount of chloroform and powderized with n-hexane. The solvent was evaporated off under reduced pressure, and the residue was held at room temperature under reduced pressure to remove the solvent adequately, whereby Compound o (528 mg, 66.6%) was obtained as greenish blue powder.

REFERENCE EXAMPLE 3

7-N-(3-methanesulfonyloxypropyl)mitomycin D (Compound p)

98 mg of 7-N-(3-hydroxypropyl)mitomycin D was dissolved in anhydrous pyridine (2 ml) and methanesulfonyl chloride (39 μl) was added thereto with ice-cooling and stirring. 3 hours thereafter, the reaction solution was diluted with ethyl acetate (50 ml) and poured in a saturated aqueous solution of sodium bicarbonate. After removal of the ethyl acetate layer, the sodium bicarbonate solution layer was twice extracted with 50 ml of ethyl acetate. The ethyl acetate layers were combined, washed with a saturated aqueous sodium bicarbonate the same manner as above are shown in Table 18, and IR and NMR of these compounds in Table 19.

TABLE 18

Synthesis and physical properties of typical Compounds (IV)

| Compound | Starting materials | | Yield (%) | M.P. (°C.) | MS (SI) | M. formula M. weight |
|---|---|---|---|---|---|---|
| | Mitomycin | Amine | | | | |
| l *1 | Mitomycin A | Br(CH$_2$)$_2$NH$_2$.HBr | 21.4 | — | m/z 442 (C$_{17}$H$_{21}$N$_4$O$_5$$^{79}$Br + 2) | C$_{17}$H$_{21}$N$_4$O$_5$Br 441 |
| m *2 | Mitomycin A | Cl(CH$_2$)$_2$NH$_2$.HCl | 83.6 | — | m/z 397 (C$_{17}$H$_{21}$N$_4$O$_5$$^{35}$Cl + 1) | C$_{17}$H$_{21}$N$_4$O$_5$Cl 396.5 |
| n *2 | Mitomycin A | Cl(CH$_2$)$_3$NH$_2$.HCl | 84.8 | — | m/z 412 (C$_{18}$H$_{23}$N$_4$O$_5$$^{35}$Cl + 2) | C$_{18}$H$_{23}$N$_4$O$_5$Cl 410.5 |
| o | Mitomycin B | Cl(CH$_2$)$_2$NH$_2$.HCl | 66.6 | >300 | m/z 398 (C$_{17}$H$_{21}$N$_4$O$_5$$^{35}$Cl + 2) | C$_{17}$H$_{21}$N$_4$O$_5$Cl 396.5 |
| p *3 | — | — | — | 112–120 | m/z 472 (M$^+$ +2) | C$_{19}$H$_{26}$N$_4$O$_8$S 470 |
| q | Mitomycin A | 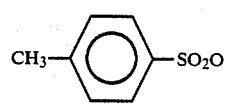 | 47.9 | 76–80 | m/z 590 (M$^+$ +2) | C$_{28}$H$_{36}$N$_4$O$_8$S 588 |
| r | Mitomycin A | Br(CH$_2$)$_8$NH$_2$.HCl | 36.0 | 64–68 | m/z 525 (C$_{23}$H$_{33}$N$_4$O$_5$$^{79}$Br + 1) | C$_{23}$H$_{33}$N$_4$O$_5$Br 525 |

*1 M.P. is not measured due to instability of the Compound.
*2 disclosed in Japanese Published Unexamined Patent Application No. 92288/81.
*3 Please refer to Reference Example 3.

TABLE 19

IR and NMR data of typical Compounds (IV)

| Compound | IR (cm$^{-1}$) | NMR ($\delta$) |
|---|---|---|
| o | 3280, 1702, 1628, 1599, 1544, 1508, 1477, 1328, 1109, 1054, 756 | (400MHz) 2.00(3H, s), 2.13(3H, s), 2.24(1H, dd, J=4.7, 2.0), 2.48(1H, d, J=4.7), 3.67(1H, dd, J=12.9, 2.0), 3.70(2H, t, J=5.9), 3.84(2H, q, J=6.3), 4.23(1H, dd, J=10.0, 3.5), 4.41 (1H, d, J=12.9), 5.21(1H, t, J=10.3), 5.47(1H, dd, J=10.5, 3.5), 7.24(1H, t, J=6.5), 7.50(2H, bs), ~8.7(1H, bs) |
| p | 3300, 1717, 1630, 1600, 1550, 1513, 1469, 1451, 1331, 1169, 1056, 930 | (400MHz) 1.93(2H, quint, J=6.4), 2.03(3H, s), 2.13(3H, s), 2.24(1H, dd, J=4.7, 1.9), 2.48(1H, d, J=4.7), 3.29(3H, s), 3.62(2H, q, J=6.8), 3.69(1H, dd, J=12.9, 1.9), 4.22(1H, dd, J=10.0, 3.4), 4.41(2H, t, J=6.0), 4.44(1H, d, J=12.9), 5.22(1H, t, J=10.3), 5.46(1H, dd, J=10.5, 3.4), 7.05(1H, t, J=6.5), ~7.5(2H, bs), 8.36(1H, bs) |
| q | 3300, 2940, 1719, 1630, 1596, 1550, 1510, 1447, 1327, 1170, 1058 | (400MHz) 1.1–1.3(4H, m), 1.38(2H, quint, J=7.1), 1.55(2H, quint, J=6.5), ~2.1(1H), 2.11(3H, s), 2.25(3H, s), 2.76(1H, bs), 3.15(1H, bd, J=4.0), 3.23(3H, s), 3.39(2H, q, J=6.8), 3.63(1H, bd, J=12.7), 4.01(1H, dd, J=11.1, 4.2), 4.14(2H, t, J=6.4), 4.57(1H, d, J=12.7), ~5.1(1H), 5.40(1H, dd, J=10.4, 4.2), 6.90(1H, t, J=6.2), 7.33(2H, d, J=8.1), ~7.6 (2H, bs), 8.02(2H, d, J=8.1) |
| r | 3300, 2930, 1717, 1631, 1603, 1552, 1510, 1465, 1447, 1326, 1059 | (400MHz) 1.1–1.3(6H, m), 1.31(2H, quint, J=7.2), 1.48(2H, quint, J=7.2), 17.4(2H, quint, J=7.1), ~2.1(1H), 2.15(3H, s), 2.76(1H, dd, J=4.4, 1.9), 3.15(1H, d, J=4.4), 3.23(3H, s), 3.41(2H, t, J=6.8), 3.47(2H, q, J=6.9), 3.62(1H, dd, J=12.7, 1.9), 4.01(1H, dd, J=11.2, 4.2), 4.57(1H, d, J=12.7), 5.06(1H, t, J=10.8), 5.40(1H, dd, J=10.4, 4.2), 6.97(1H, t, J=6.1), ~7.6(2H, bs) | solution and with a saturated aqueous sodium chloride solution, and dried over anhydrous sodium sulfate. After the drying agent was removed by filtration, the solvent was evaporated off under reduced pressure. The residue was chromatographed over silica gel (40 g) in a column. Elution was effected with chloroform/methanol (9:1) and the blue fractions exhibiting an Rf value of 0.32 in TLC developed with the same solvent system as above were collected and combined. The solvent was evaporated off under reduced pressure and the residue was held at room temperature under reduced pressure to remove the solvent adequately, whereby Compound p (47.3 mg, 40.3%) was obtained as grayish green powder.

Starting materials, yield, M.P. and MS of Compounds o and p and Compounds l, m, n, q and r synthesized in

We claim:
1. Mitomycin compounds represented by the following formula:

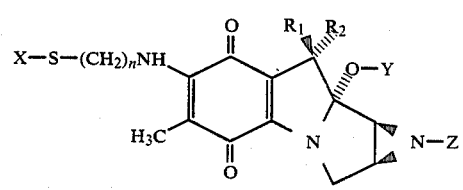

wherein X is

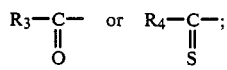

wherein $R_3$ is an alkyl group having 1 to 8 carbon atoms, a 3–6 membered cycloalkyl group, or a phenyl group optionally bearing 1 or 2 substituents selected from lower alkyl, hydroxy, lower alkoxy, nitro, lower alkylamino, di-lower alkylamino, lower alkanoylamino, cyano or halogen; and $R_4$ is an alkyl group having 1 to 8 carbon atoms or a 3–6 membered cycloalkyl group; n is an integer of 2 to 8; one of $R_1$ $R_2$ is a hydrogen atom and the other is a carbamoyloxymethyl group, or alternatively $R_1$ and $R_2$ may be combined together to form a methylene group (=CH$_2$); and Y and Z independently represent hydrogen or methyl.

2. Mitomycin compounds according to claim 1 wherein X is

and $R_3$ is an alkyl group having 1 to 4 carbon atoms.

3. Mitomycin compounds according to claim 2 wherein $R_3$ is a methyl group or an ethyl group.

4. Mitomycin compounds according to claim 3 wherein n is 2 or 3.

5. Mitomycin compounds according to claim 1 wherein $R_3$ is a substituted phenyl group bearing 1 or 2 substituents.

6. A pharmaceutical composition containing a pharmacologically effective amount of a mitomycin compound of any of claims 1 to 5 and at least one pharmaceutically acceptable carrier and/or excipient.

* * * * *